(12) United States Patent
Schwartz

(10) Patent No.: US 9,943,443 B2
(45) Date of Patent: Apr. 17, 2018

(54) PAIR OF EYE GOGGLES

(71) Applicant: Alan N. Schwartz, Edmonds, WA (US)

(72) Inventor: Alan N. Schwartz, Edmonds, WA (US)

( * ) Notice: Subject to any disclaimer, the term of this patent is extended or adjusted under 35 U.S.C. 154(b) by 177 days.

(21) Appl. No.: 14/828,476

(22) Filed: Aug. 17, 2015

(65) Prior Publication Data

US 2015/0351964 A1 Dec. 10, 2015

Related U.S. Application Data

(63) Continuation of application No. 13/683,775, filed on Nov. 21, 2012, now Pat. No. 9,107,737.

(60) Provisional application No. 61/562,382, filed on Nov. 21, 2011.

(51) Int. Cl.
| | |
|---|---|
| *A61F 9/02* | (2006.01) |
| *G02C 5/12* | (2006.01) |
| *A63B 33/00* | (2006.01) |
| *G02C 3/00* | (2006.01) |
| *A61M 16/04* | (2006.01) |
| *A61M 16/06* | (2006.01) |
| *B63C 11/12* | (2006.01) |

(52) U.S. Cl.
CPC ............. *A61F 9/02* (2013.01); *A61F 9/026* (2013.01); *A61F 9/027* (2013.01); *A61F 9/029* (2013.01); *G02C 3/003* (2013.01); *G02C 5/12* (2013.01); *A61M 16/04* (2013.01); *A61M 2016/0661* (2013.01); *A63B 2033/004* (2013.01); *A63B 2209/00* (2013.01); *B63C 2011/128* (2013.01); *G02C 2200/16* (2013.01)

(58) Field of Classification Search
CPC .. A61F 9/02; A61F 9/029; A61F 9/026; A61F 9/027; A63B 33/002; A63B 2033/004; A63B 2033/006; A63B 2033/008; B63C 11/12; B63C 2011/121; B63C 2011/128; G02C 5/122; G02C 5/124; G02C 5/126; G02C 5/12; G02C 3/003; G02C 2200/16; A61M 2016/0661
USPC ............ 2/445, 446, 440, 442, 453, 452, 454
See application file for complete search history.

(56) References Cited

U.S. PATENT DOCUMENTS

| | | | |
|---|---|---|---|
| 1,190,123 A * | 7/1916 | Day ....................... | A61F 9/029 2/446 |
| 1,295,128 A * | 2/1919 | Day ....................... | A61F 9/025 2/445 |
| 1,306,549 A * | 6/1919 | Malcom .................. | A61F 9/025 2/441 |
| 1,526,793 A | 2/1925 | King | |
| 2,979,729 A | 4/1961 | Hirschmann, Jr. | |

(Continued)

*Primary Examiner* — Amy Vanatta
(74) *Attorney, Agent, or Firm* — Patrick J. S. Inouye

(57) ABSTRACT

A pair of eye goggles is described. The eye googles include a three axial adjustable nosepiece that can be fit over a wearer's nose including a plurality of unequal length strands on each side of the nosepiece with the strands comprising resilient properties different from the resilient properties included in the other strands in the plurality of strands on that side. The eye goggles also include a strap that can be fit removably around the wearer's head, and a pair of eyepieces. Each eyepiece includes a transparent lens that can be fit over one of the wearer's eyes, and a frame that surrounds the transparent lens to which the nosepiece and the strap are attached. The eye goggles also include a sealing pad formed on an inside-facing edge of the frame.

8 Claims, 21 Drawing Sheets

(56) References Cited

U.S. PATENT DOCUMENTS

| | | | | |
|---|---|---|---|---|
| 3,712,714 A | * | 1/1973 | Uyeda | B63C 11/12 2/428 |
| 4,264,987 A | | 5/1981 | Runckel | |
| 5,187,871 A | * | 2/1993 | McDermott | B63C 11/12 2/430 |
| 5,191,317 A | * | 3/1993 | Toth | B63C 11/12 128/201.22 |
| 5,390,373 A | * | 2/1995 | Flory | A63B 33/002 2/430 |
| 5,502,844 A | | 4/1996 | Alvarado | |
| 5,560,047 A | * | 10/1996 | Shimada | A42B 1/12 2/428 |
| 5,857,221 A | | 1/1999 | Geneve et al. | |
| 6,119,277 A | | 9/2000 | Chiang | |
| 6,119,279 A | | 9/2000 | Haslbeck | |
| 6,247,187 B1 | | 6/2001 | Chiang | |
| 6,289,523 B1 | | 9/2001 | Chiang | |
| 6,349,417 B1 | | 2/2002 | Chiang | |
| 6,447,115 B1 | * | 9/2002 | Gallagher | B63C 11/12 351/158 |
| 6,530,093 B1 | | 3/2003 | Chiang | |
| 6,883,184 B2 | | 4/2005 | Lee | |
| 7,143,454 B2 | | 11/2006 | Kawashima et al. | |
| 7,823,225 B2 | | 11/2010 | Chou | |
| 2001/0034896 A1 | | 11/2001 | Chiang | |
| 2002/0170108 A1 | | 11/2002 | Chiang | |
| 2002/0176323 A1 | * | 11/2002 | Magine | B63C 11/26 367/134 |
| 2004/0187196 A1 | * | 9/2004 | Haslbeck | A63B 33/002 2/426 |
| 2004/0187197 A1 | | 9/2004 | Chiang | |
| 2008/0301859 A1 | * | 12/2008 | Chou | A63B 33/002 2/445 |
| 2009/0059501 A1 | * | 3/2009 | Yamaguchi | A61F 9/029 361/679.27 |
| 2010/0083425 A1 | | 4/2010 | Miller | |
| 2010/0302233 A1 | * | 12/2010 | Holland | B63C 11/12 345/419 |
| 2016/0223338 A1 | * | 8/2016 | Lassen | G01S 19/19 |

* cited by examiner

PAIR OF EYE GOGGLES

CROSS-REFERENCE TO RELATED APPLICATION

This non-provisional patent application is a continuation of U.S. Pat. No. 9,107,737, issued on Aug. 18, 2015, which claims the benefit of U.S. Provisional Patent Application Ser. No. 61/562,382, filed Nov. 21, 2011, the disclosures of which are incorporated herein by reference in their entireties.

COPYRIGHT NOTICE

Notice is hereby given that the following patent document contains original material which is subject to copyright protection. The copyright owner has no objection to the facsimile or digital download reproduction of all or part of the patent document, but otherwise reserves all copyrights whatsoever.

FIELD

This invention pertains to goggles and more particularly to goggles designed to conform to the user's eye sockets and facial features.

BACKGROUND

For swimmers, finding goggles that properly fit and provide a watertight seal against the face is important. Unfortunately, it is estimated that approximately 50% of commonly worn goggles provide a watertight seal. While some goggles are designed to address the watertight problem by using seals made of gel material to create a watertight seal, these goggles do not address the problem of eye spacing variations and the anatomical facial differences of the users that cause poor fitting goggles.

For example, one variation is the distance between the user's pupils and eyes and orbital sockets. Some individuals have less distance between their pupils, eyes, and orbits compared to the norm, which is commonly known as hypotelerism. Other individuals have greater distance between their pupils, eyes, orbits compared to the norm, which is known as hypertelerism. Unfortunately, most goggles commonly available today are 'one size fits all' and have fixed length nosepieces that hold the eyepieces apart at a fixed distance for most wearers.

The primary purpose of a nosepiece on a goggle is to hold the two eyepieces in place over the users' eyes. While some goggles include nosepieces that enable the user to selectively adjust the distances between the eyepieces, they do not allow the eyepieces to be independently adjusted to conform to the adjacent eye socket or anatomical features.

SUMMARY

The current invention is a goggle that includes a strap configured to wrap around the user's head and two eyepieces affixed or mounted to the strap. Each eyepiece includes an outer transparent lens and a surrounding rigid or flexible frame. The two eyepieces, which may be made of rigid or flexible material, are coupled together by a nosepiece that allows the distances between the eyepieces to be adjusted and allows the eyepieces to independently flex and rotate over the eye socket and conform to the surrounding tissue. The nosepiece provides for some give and elasticity to allow the eyepieces to flex, move and conform to the user's facial contours.

The invention provides for the following characteristics: independent nosepiece that provides 3-axial movement; a conforming nosepiece; and an adjustable strap.

The nosepiece disclosed herein can have various shapes and various attachment means to the eyepieces or to the strap. In one embodiment, the nosepiece is made of one or more elastic strands that have the same or different elastic properties and lengths. The strands may be attached at its opposite ends to the eyepieces or to intermediate connectors that attach to the eyepieces.

The goggle may also include an optional sealing pad configured to press against and conform its shape to the user's skin around each eye to form a watertight seal. In one embodiment, the sealing layer is made of gel material. In another embodiment, the thickness of the sealing layer varies so that it is thinner and adjacent to the user's bridge and thicker along its outer edges.

It should also be understood, that the invention can also be used as a generic closure device that provides for flexibility and elasticity of the eyepieces. The closure device can but is not restricted to, a nosepiece such that the eyepieces can flex and move with the user's facial contours and movements and have a greater range of conformity than current joints. In one embodiment, the invention will be for use with living creatures to include but not restricted to humans and other animals but can also be used with inanimate objects. The closure device can also be used with a gel seal cast and wound cover. The closure device can help insure that the gel is fixed in place during vigorous activities, yet the closure can flex to conform to muscle contractions and expansions and can replace fixed compression closure devices that may reduce venous and arterial blood flow.

In another embodiment, the invention includes a flex layer which acts as a transitional layer between the goggle's rigid, semi-rigid or flexible frame and the sealing pad. The flex layer is designed to automatically adjust its shape to the orbit. The flex layer is composed of a material that is resiliently deformable and can expand or contract to the users face in a manner that differs from the sealing layer and the frame. The flex layer has characteristics that differ from the frame and the sealing pad.

Also disclosed herein is a tester used to assist the purchaser in choosing the 'best fit' goggle. The tester includes a gel in the shape of an obit that is pressure sensitive and designed to change color to display the degree of pressure and thickness required to create and airtight and watertight seal. When pressed against the orbit, the gel will change color at different pressure points. In one embodiment, the color displayed on the tester can then be compared to a color code that is printed on packaging. The consumer can then more reliably find a pair goggles that will likely conform to their face to form an airtight and watertight seal.

One embodiment provides a pair of eye goggles. The eye googles include a three axial adjustable nosepiece that can be fit over a wearer's, nose including a plurality of unequal length strands on each side of the nosepiece with the strands comprising resilient properties different from the resilient properties included in the other strands in the plurality of strands on that side. The eye goggles also include a strap that can be fit removably around the wearer's head, and a pair of eyepieces. Each eyepiece includes a transparent lens that can be fit over one of the wearer's eyes, and a frame that surrounds the transparent lens to which the nosepiece and the strap are attached. The eye goggles also include a sealing pad formed on an inside-facing edge of the frame.

BRIEF DESCRIPTION OF THE DRAWINGS

In FIG. 19A, the user's face/body part is initially stationary and the imaging devices are placed in strategic positions around the users face/body part. In this embodiment, the user's face/body part can rotate or move relative to the cameras or imaging devices. There can be one or more than one imaging device. The imaging devices can include but are not restricted to cameras that utilize electromagnetic Energy such as visible light. In another embodiment the imaging device can include kinetic Energy or vibrational or ultrasound imaging devices or combination of electromagnetic and mechanical and vibrational and kinetic energy.

In FIGS. 19B and 19C, the user's face/body part is stationary and the imaging device can rotate or move 100 relative to the user's face/body part. In another embodiment, the user's face/body part is stationary and imaging device can have components that allow the energy propagation to begin at one position and rotate or move to a different position.

FIG. 20A is the edge of a material onto which there is an attachment device. This is primary attachment device has numerous flanges or bristles or outcroppings. The orientation of the outcroppings were flanges or bristles is such that what a second attachment device is placed into the hollow of the first attachment device it can be restrained from moving out of the hollow of the first attachment device by a series of flanges or bristles or outcroppings that are oriented in the same direction as the primary attachment device hollow flanges or bristles or outcroppings. FIG. 20A also demonstrates an elastomeric strand or band or closure device attached to the secondary attachment device. When a force is placed away from the attachment device or strand or band or closure device the strand or band or closure device can stretch but the secondary attachment device remains fixed within the first or primary attachment device.

FIG. 20B Is a representation of there-secondary attachment device being removed from the primary attachment device by squeezing or putting pressure force on the secondary attachment device such that the distance between the components of the secondary attaching device are narrowed and the bristles were outcroppings or flanges can be removed from the hollow of the primary task device.

In FIG. 21A, there is a metallic wire embedded within the elastic strand. The wire can be undulating or coiled and as the elastic strand expands the wire will limit or govern the maximal stretch of the strand or band or closure device in the x axis but will not alter the movement in the y axis or the z axis or both the y and z axes when subjected to a force which can include but is not restricted to a distraction or a pulling or pushing force.

In FIG. 21B there is a composite material that is embedded within the elastic strand or band or closure device and the composite material has a geometric shape that will limit the strand or band or closure device in one or more than one of its axes when subjected to a force which can include but is not restricted to a distraction or a pulling or pushing force.

FIG. 22A is a representation in which the attachment piece is annular and elastomeric strand or band or closure device is fitted into the annular attachment piece using a coupling device.

FIG. 22B is an illustration in which the attachment piece is slotted and contains a screw and a flat coupling device that is compressed against the wall of the slotted attachment piece and the elastic strand or band or closure device is attached to the flat transitional coupling device.

FIG. 22C is an illustration showing a solid key coupling device being placed into a hole in the attachment piece and multiple of elastic strand or band or closure device are attached to the coupling device.

In FIGS. 24A-D, the strand or band or closure device can be of different sizes thicknesses and shapes.

In FIGS. 24E-G, the strand or band or closure device can have different elastomeric qualities of the strand or band or closure device and each can have a recognizable method and means of designating the different elastomeric bands which can include but is not restricted to color or texture or shape. In this example the bands are designated as different colors red green and blue.

In FIG. 25A, the attachment device can contain one or more partitions. The partitions can also include one or more slits for allowing the elastic strand or band or closure device to fit into the attachment piece partitions.

In FIG. 25B, the attachment device can be angled to allow for a better fit or contour particularly near a body part structure that protrudes, such as the nose.

FIG. 26A shows a movement element that can be a slot incorporated into the attachment device in which a coupling device is attached to the elastomeric strand or band or closure device and which can be continuous and can be fitted into the slot. The coupling device and the attachment device can then move freely relatively to each other within the slot and assist the strand or band or closure device to conform to the user's body contour or ergonomics and movements and forces.

FIG. 26B is a representation of an attachment device with an elastic strand or band or closure device that fits into a circular movement device within the attachment device of the object being bridged or closed or connected.

FIG. 26C is an attachment device that is angulated and has a single movement point of motion relative to the attachment device and elastic strand or band or closure device.

FIG. 26D is a test of device that has more than a single movement point in response to motion relative to the attachment device and the elastic strand or band or closure device And can incorporate one or more than one coupling devices to facilitate the motion.

FIG. 27 demonstrates three embodiments. The first embodiment includes an area that is cut out of the mask/goggle that can contain the elastomeric strand or band or closure device and attachment devices. In another embodiment the attachment device and strand or band or closure device can be on the surface of the mask or goggle on the side opposite of the users skin/face. In another embodiment the attachment device and elastic strand or band or closure device can lie on the surface of the mask/goggle on the side between uses face and the mask/goggle. In another embodiment the elastic strand or band or closure device can be embedded or incorporated into the mask or goggle.

FIG. 28A demonstrates a plastic belong gated hollow tube. This tube can be located and wound on his spool (not shown).

FIGS. 28B and 28C demonstrate the cast cover and an arm/body part and cast length that is calculated by a measuring device. Using the image or size and proportions measurements the proper length of the hollow tubing can be determined. Once the length of tubing is designated a portion or all of the tube can be sealed creating a watertight end of an open hollow tube that was previously open at both ends. Now the tube is closed and watertight fused or closed at one end and open at the other end. This will allow the hand cast to pass through the open-end and the tube will be precisely the correct length required to cover the cast and the body part with an airtight and watertight seal with the skin (not shown) and the fused or close end that is now airtight and watertight. The dotted line represents the site where the tube that is still attached to the role can be cut and a new opening exists that will allow for a new cast cover to be created.

FIG. 28C demonstrates the final product with a cast cover with its airtight and watertight seal in place, which is at the optimal length for the cast cover and the hollow tube is ready for creating another cast cover segment.

DETAILED DESCRIPTION

Figure 1:
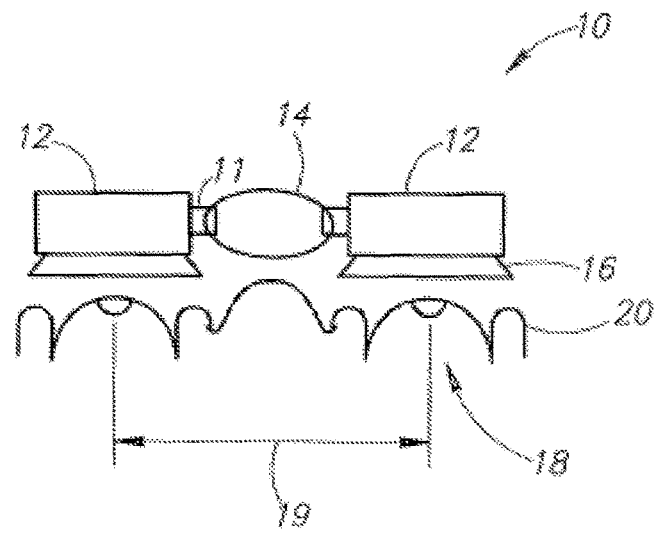
FIG. 1 depicts a nosepiece that fits between the two eyepieces of the goggle and provides for both stability and variations is the distance between the user's pupils, eyes and orbital sockets. The nosepiece is annular in this diagram.

Referring to FIG. 1, there is shown a goggle (10) with eyepieces that are individually custom-fitted over the user's his or her eye sockets. The goggle (10) includes a strap, two face-conforming eyepieces connected or affixed to connection points on the strap and an adjustable nosepiece that extends between the two eyepieces and over the user's bridge. An optional sealing layer is also provided on each eyepiece to provide confirming watertight seal around each eyepiece. The nosepiece is made of one or more elastic strands that have the same or different resilient properties. The ends of the strands may be attached to connectors mounted on the inside edges of the two eyepieces or integrally formed on the strap. During use, the strap holds the eyepieces in place while the user then adjusts the nosepiece by selecting a suitable number of strands with the same or different lengths and with the same or different resilient properties, so that the eyepieces may be independently aligned themselves over the eye sockets and form a comfortable, watertight seal against the surrounding facial tissues.

FIG. 1 shows one embodiment of the goggle (10) that includes a nosepiece (14) that fits between the two eyepieces (12) and provides for both stability and variations is the distance between the user's pupils (19), eyes and the size and depth of the orbital sockets (18). The nosepiece (14) also provides for stretch, such that the eyepieces (12) can flex and move with the user's facial (20) contours and movements and have a greater range of conformity than the current nosepieces (14). The nosepiece (14) can be but is not restricted to an elastomeric, resiliently, deformable material that can include but is not restricted to a solid or gel or a combination of a solid or gel. The elastomeric material can have variable elasticity within different portions of the nosepiece (14) which can include but is not restricted to one embodiment, where the nosepiece (14) is more elastic at the center of the nosepiece (14) than at its periphery, near the eyepiece (12). In another embodiment, the nosepiece (14) is non-uniform with it being more elastic at the periphery, near the eyepiece (12) than at the center of the nosepiece (14). In another embodiment, the nosepiece (14) can be more elastic near the face (20) away from the face (20). In still another embodiment, the nosepiece (14) can be more elastic away from the face (20) than near the face (20).

In FIG. 1, the nosepiece (14) can be different lengths to accommodate the different distances between the pupils, eyes and orbits, The nosepiece (14) can be formed from a material that can be optimized to the individual user will maintain its length and form fit the user. In another embodiment the nosepiece (14) can include but is not restricted to a gel or solid that can be molded or fixed or cured in shape to an optimized length and fit include but not restricted to chemical reaction, mechanical reaction, heating, cooling, or electromagnetic energy to include bit not restricted to Ultraviolet or infrared energy.

In FIG. 1, another embodiment, fixed and variable flexibility nosepieces (14) can be used together or separately or in combination. Materials that can be used for form fitting can include but are not restricted to thermo-sensitive solids and gels that can include but are not restricted to thermo-sensitive-plastics, gels, metals to include but not restricted to polystyrenes, Nitenol, moldable metals composed of composed of common metals like copper, nickel, titanium and zirconium and hand moldable plastics.

In another embodiment, a portion or all of the nosepiece (14) can be composed of the phase transitional materials and phase transitional slurry that can be macro-encapsulated or micro-encapsulated.

In FIG. 1, in another embodiment, there can be a fixed or flexible or a variable flexibility to the eyepiece (12) that can be used together or separately or in combination. Materials that can be used for form fitting can include but are not restricted to thermo-sensitive solids and gels that can include but are not restricted to thermo-sensitive-plastics, gels, metals to include but not restricted to polystyrenes, Nitenol, moldable metals composed of composed of common metals like copper, nickel, titanium and zirconium and hand moldable plastics.

In FIG. 1, another embodiment can include a nosepiece (14) where at least a portion of the nosepiece (14) is elastic.

In FIG. 1, another embodiment can include a nosepiece (14) where at least a portion of the nosepiece (14) is moldable to the unique features of the user's eyes (18) and face (20).

In FIG. 1, another embodiment can include an eyepiece (12) where at least a portion of the eyepiece (12) is elastic.

In FIG. 1, another embodiment can include an eyepiece (12) where at least a portion of the eyepiece (12) is moldable to the unique features of the user's eyes (18) and face (20).

In FIG. 1, another embodiment can include a seal (16) where at least a portion of the seal (16) is moldable to the unique features of the user's eyes (18) and face (20).

In FIG. 1, the nosepiece (14) can be annular.

Figure 2A:
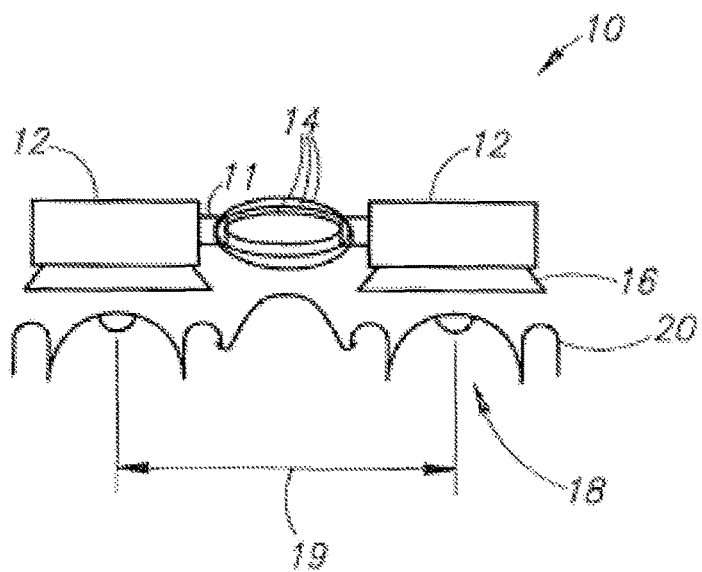
FIG. 2A depicts a nosepiece in which the nosepiece can be formed from one or more than one nosepiece elements. The nosepiece elements can be of the same or of differing elasticity. The nosepiece elements can be formed of the same length or different lengths.
Figure 2B:
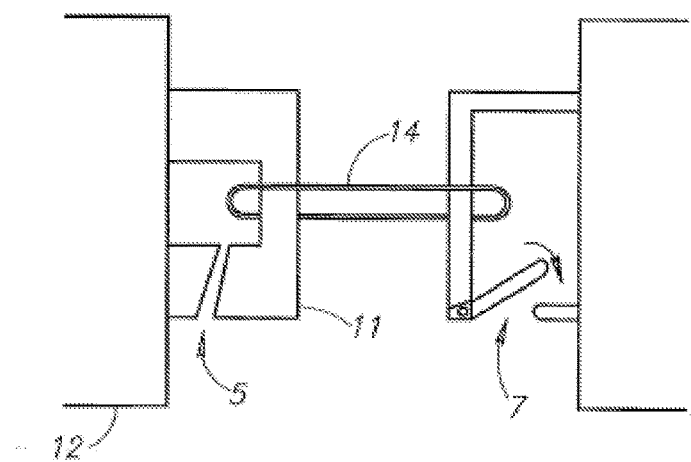
FIG. 2B depicts a nosepiece attachment entry in which the nosepiece attachment entry can have many forms to include but not restricted to a slit, teacup-hook-like configuration, gate-like entry, a straight or a seripinginous channel, a hook-like configuration or a valve. The numerous strands shown in FIG. 2C readily allow the user to adjust the spacing and elasticity to allow the user to create and select the best fit using single or multiple bands between the two eyepieces. The plethora of possible adjustments to the nosepiece described above results, for all practical purposes, in the amount of stretch of the nosepiece being continuously adjustable by the user.
Figure 2C:
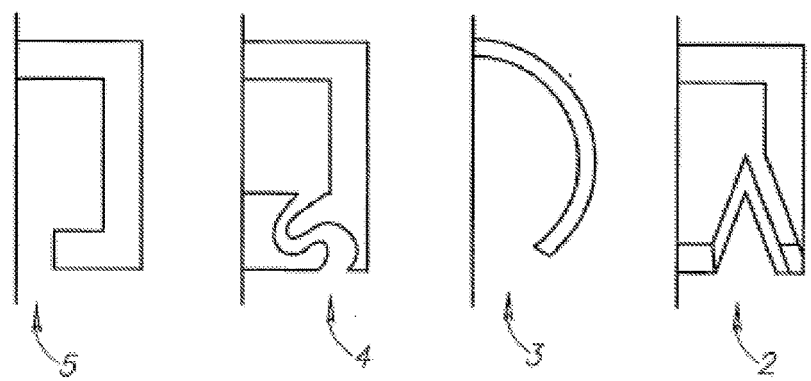

In FIG. 2A, the connecting element forming the nosepiece (14) between the eyepieces (12) can be formed from one or more than one nosepiece (14) elements. The nosepiece elements (14) can be of the same or of differing elasticity. The nosepiece (14) elements can be formed of the same length or different lengths.

In 2B and 2C, the nosepiece (14) can have various shapes and forms of attachment. The preferred embodiment is an annular nosepiece (14) that fits into an annular nosepiece attachment (11) that has a slit that allows the nosepiece to fit securely into the hollow of the annular eyepiece. The security of the nosepiece attachment (11) can be either by placing the nosepiece in a stretched and thinned position such that the nosepiece (14) will fit through the nosepiece (12) slit (5) and when the nosepiece (14) is in the non stretched position the nosepiece (14) diameter will be greater than the length of the nosepiece (14) slit. Another embodiment is a teacup-hook type (7) attachment. Variations in attachment entries can include but not restricted to a slit (5), teacup-hook-like configuration or gate-like entry (7), a straight (5) or a seripinginous channel (4), various geometric hook-like configurations (3) or a valve or flap (2) or any combination or these entries and configurations.

Figure 3:
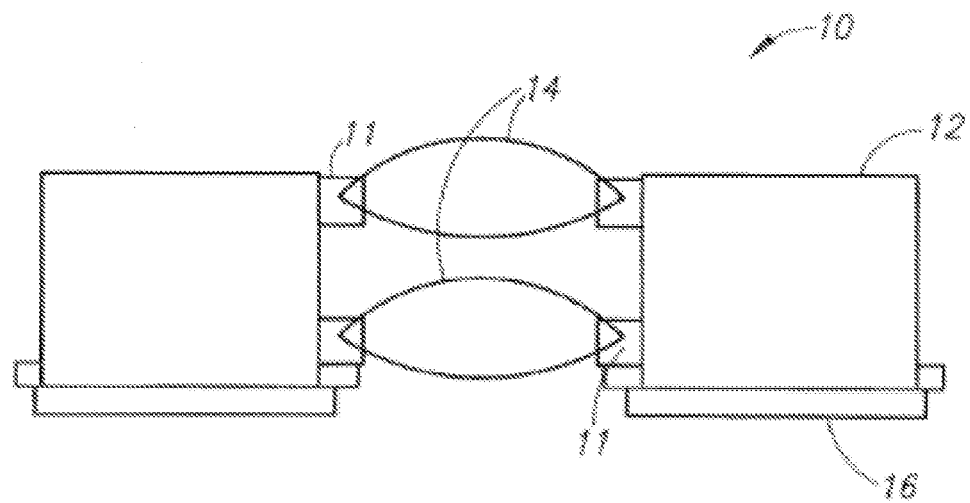
FIG. 3 depicts a nosepiece where the nosepiece attachment to the eyepiece can attach to one or multiple locations. The location of the nosepiece attachment can vary in their position on the eyepiece. The nosepiece attachment can vary in its position and height.

In FIG. 3, the nosepiece (14) can attach to the eyepiece (12) in one or multiple locations. The location of the nosepiece attachment (11) can vary in their position on the eyepiece (12). The nosepiece attachment (11) can vary in its position and height.

In FIG. 3, the nosepiece (14) can be elastic. The nosepiece (14) can have variable elasticity.

In FIG. 3, the nosepiece (14) in the preferred embodiment is annular. The annular nosepiece (14) can be elastic or non-elastic or a combination of elastic and non-elastic. The annular nosepiece (14) can be moldable.

Figure 4:
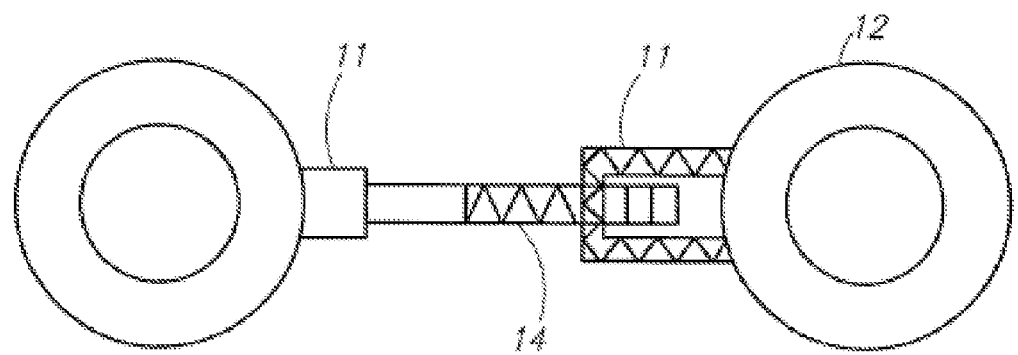
FIG. 4 depicts a nosepiece that can be non-annular. The non-annular nosepiece can be elastic or non-elastic.

In FIG. 4, the nosepiece (14) can be non-annular. The non-annular nosepiece (14) can be elastic or non-elastic. If it is non-elastic is can be moldable to produce a unique fit to the user's inter-papillary distance, eyes (18) and face (20).

The elasticity can vary relative to its attachment position on the eyepiece. The nosepiece (14) can be more elastic near the center of the nosepiece (14) away from the eyepiece (12). The nosepiece (14) elasticity can be more elastic near the eyepiece (12). The nosepiece (14) elasticity can be a combination of more elastic near the center away from the eyepiece (12) and near the eyepiece.

In FIG. 4, the nosepiece attachment (11) can be elastic. If the nosepiece attachment is elastic then the nosepiece (14) can be either elastic or non-elastic. The nosepiece (14) can be attached permanently to the nosepiece attachment or it can be non-permanently attached and can include but not restricted to it being removable or interchangeable.

Figure 5A:
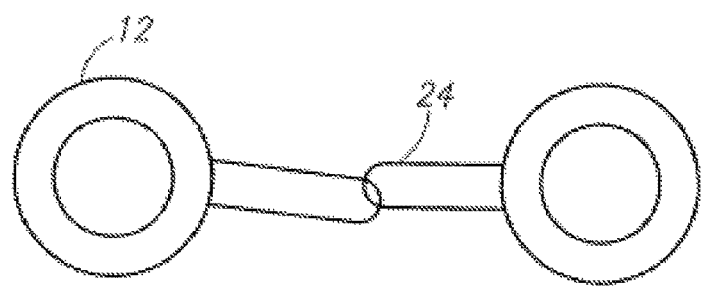
FIG. 5A depicts two eyepiece attachments that can connect to each other without a separate connection nosepiece.

In FIG. 5A, there can be one, two or multiple eyepiece attachments (24) that can connect to each other without a separate connection nosepiece. The eyepieces (12) can have different and multiple geometric shapes other than that of a circle, which can include but are not restricted to multiple circles, polygons to include but not restricted to triangles squares, pentagons hexagons and other multisided structures. The nosepiece (14) and eyepiece (12) together or separately can be oriented in the same plane or in different planes.

Figure 5B:
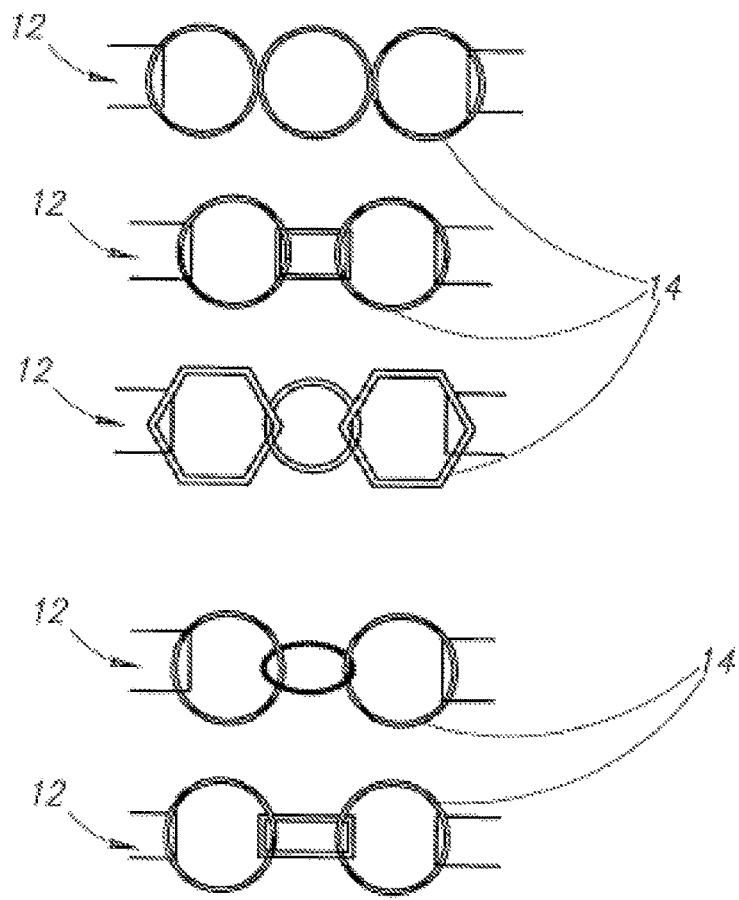
FIG. 5B depicts a nosepiece or an eyepiece that can have different and multiple geometric shapes other than that of a circle which can include but are not restricted to multiple circles, polygons to include but not restricted to triangles squares, pentagons hexagons and other multisided structures. The nosepiece and eyepiece together or separately can be oriented in the same plane or in different planes.

FIG. 5B depicts a nosepiece (14) or an eyepiece (12) that can have different and multiple geometric shapes other than that of a circle which can include but are not restricted to multiple circles, polygons to include but not restricted to triangles squares, pentagons hexagons and other multisided structures. The nosepiece (14) and eyepiece (12) together or separately can be oriented in the same plane or in different planes. The nosepieces (12) and eyepieces (14) can be annular or non-annular.

Figure 6:
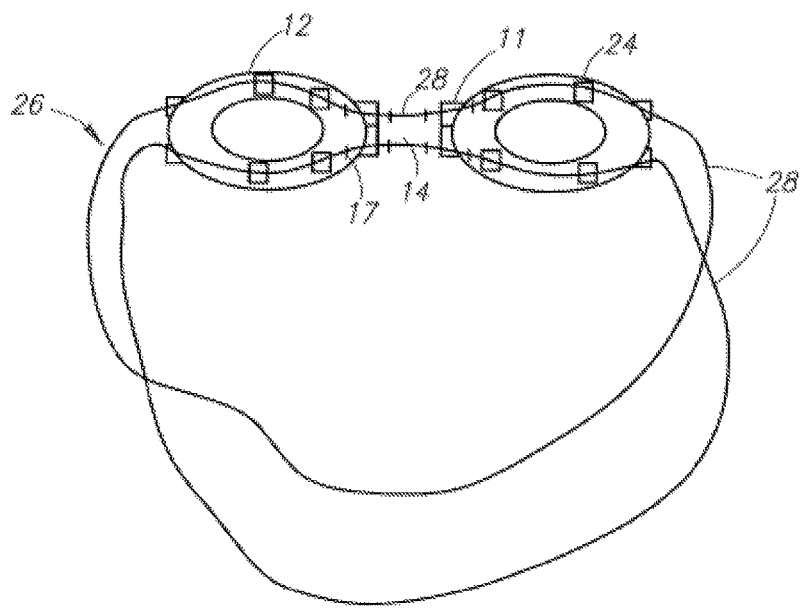
FIG. 6 depicts a nosepiece that can be constructed to be continuous with the strap, which can be formed from one or multiple combined strap-nosepiece units.

In FIG. 6, the nosepiece (14) can be constructed to be continuous with the strap (26), which can be formed from one or multiple combined strap-nosepiece (28) units. The strap-nosepiece (28) unit can attach to the eyepieces in one or multiple locations and can also be thread within the eyepiece (12) unit on one or multiple locations. The strap-nosepiece combination unit (28) can have a method for holding the intervals that keep the strap-nosepiece (28) combination unit in position and these position holders (17) can include but are not restricted to beadings, protuberances, recessions, grooves, and flanges.

Figure 7:
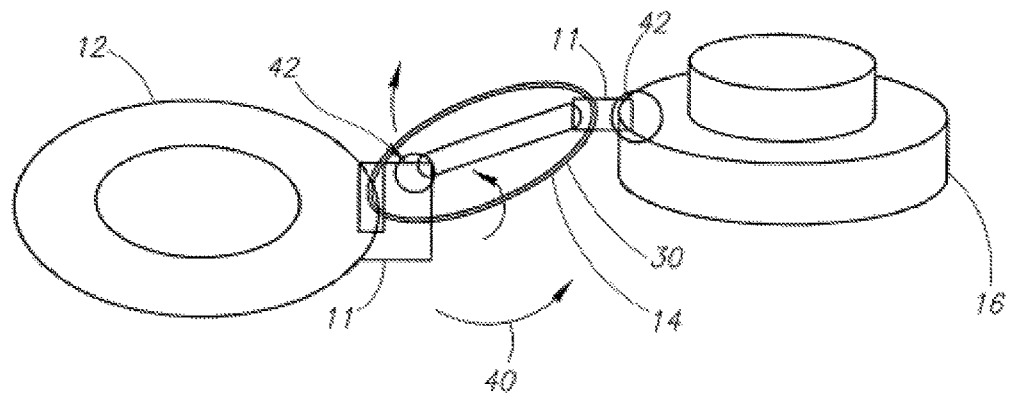
FIG. 7 depicts a nosepiece in which the connector joint provides for some give and elasticity such that the eyepieces can flex and move with the users facial contours and movements and have a greater range of conformity than current joint connectors and the connector joint or connector joint attachment can be can be constructed to be moveable to include but not restricted to rotating or swiveling.

In FIG. 7, the invention can also be used as a nosepiece (14), connector joint (30), that provides for some give and elasticity such that the eyepieces (12) can flex (40) and move with the users contours and movements and have a greater range of conformity than current joint connectors. The connector joint (30) or connector joint attachment (11) can be can be constructed to be moveable to include but not restricted to rotating or swiveling on a swiveling mechanism (42).

Figure 8:
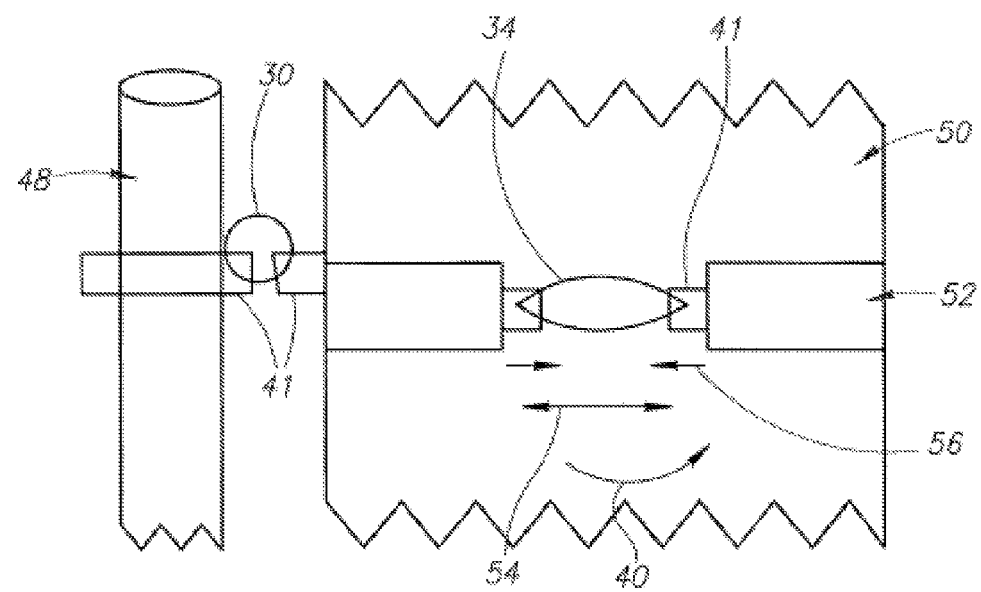
FIG. 8 depicts a joint connector that is used with a urinary catheter tube.

In FIG. 8, the joint connector (30) preferred embodiment will be for use with living creatures to include but not restricted to humans and other animals but can also be used with inanimate objects. The joint connection (30) can be used for applications other than goggles and those applications can include but are not restricted to an electronic attachment (32), medical device or apparatus attachment. Some examples of this can include but are not restricted to serving as a flexible connecting joint for a mask to a CPAP mask; a tube to include but not restricted to a urinary catheter tube (48); a bag, to include but not restricted to an ostomy bag; an electrical device to include but not restricted to an Ipod and a heart monitor, and an insulin monitoring device; as well as other objects that need to be attached to a living creature in a static or a dynamic manner.

The connector (30) can form a joint connection (30) for one or multiple items or devices that can but is not restricted to strapping or attaching or fixating one item to include but not restricted to a strap (52) to another item that can include but is not restricted to a human structure to include but not restricted to an appendage to include but not restricted to a leg (50) which in turn can be affixed to another item to include but not restricted to a urinary catheter tube (48). The connector can have the properties to include but not restricted to expanding (54), contracting (56) or flexing (40). The joint connector (30) can be attached directly to the item or it can be attached to the items with a joint connector attachment (41).

Figure 9A:
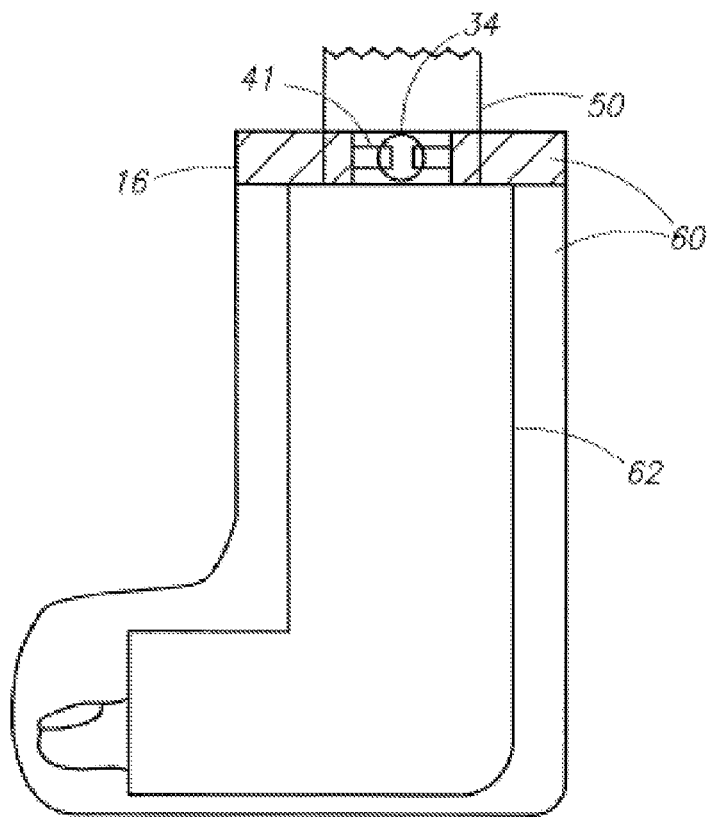
FIG. 9A depicts a closure device for a cast cover front view.

FIG. 9A, is a closure device (34) for a cast cover (36) that also provides for flexibility and elasticity of the closure device (34). The closure device (34) can be used to seal two open ends of a partially circumferential structure to make it more circumferential or fully circumferential and close the circle. The closure device (34) can assist with a seal (16) to include but not restricted to an airtight and watertight seal or can be used to more tightly press the seal (16) against the object to be sealed to include but not restricted to the skin or mucosa, or a membrane or an open cavity to include but not restricted to the leg (50) against the closure device can also be used with a seal (16) for a cast and wound cover (60), The closure devise can help insure that the gel is fixed in place during vigorous activities, yet the closure can flex to conform to muscle contractions and expansions and can replace fixed compression closure devises that may reduce venous and arterial blood flow. The closure device (34) in the preferred embodiment will be for use with living creatures to include but not restricted to humans and other animals but can also be used with inanimate objects. The closure device (34) can have the properties to include but not restricted to expanding (54), contracting (56) or flexing (40). The joint connector can be attached directly to the item or can be attached to the items with a joint connector attachment (41).

Figure 9B:
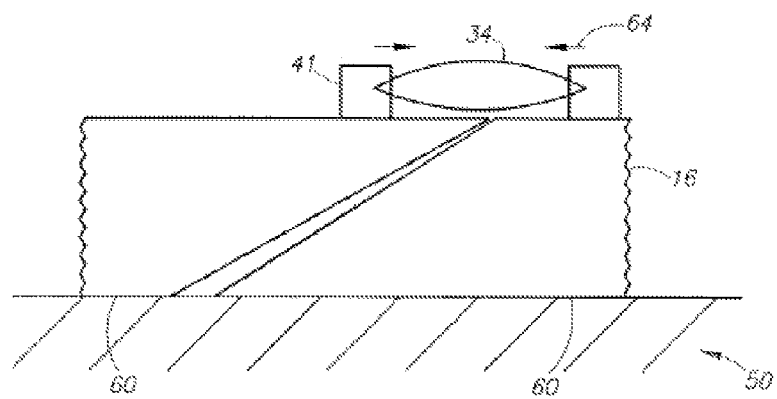
FIG. 9B, depicts the closure device for a cast such that the seal when closed and overlapping is transformed from non-circumferential to circumferential when the closure device is engaged and held under tension.

FIG. 9B, depicts the closure device (34) holding a seal (16) for a cast cover (60) for a cast (62) in place such that the seal when closed and overlapping is transformed from non-circumferential to circumferential when the closure device (34) is engaged and held under tension (64).

Figure 10:
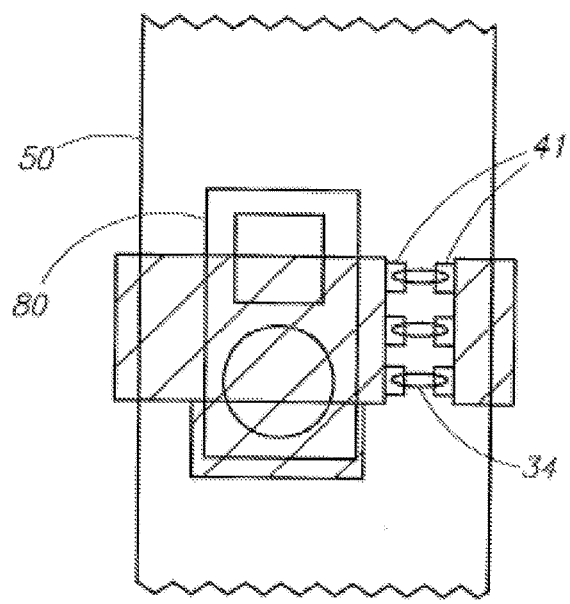
FIG. 10 depicts a closure device for holding an electrical device such as an iPod.

FIG. 10, is a closure device (34), which in the preferred embodiment can be used during activity to include but not restricted to vigorous activities. The closure can flex to conform to muscle contractions and expansions and can replace fixed compression closure devises that may reduce venous and arterial blood flow. The closure device (34) in the preferred embodiment will be for use with living creatures to include but not restricted to humans and other animals. Some examples of this can include but are not restricted to closure of bandages, wraps, holding devices to include but not restricted to an electrical device (80) to include but not restricted to an Ipod and a heart monitor, and an insulin monitoring device. The closure device (34) in the preferred embodiment will be for use with living creatures to include but not restricted to humans and other animals but can also be used with inanimate objects. This can be used to replace tight fitting restrictive closures to include but not restricted to Velcro, adhesive tape, rope, bands, and cloth to include but not restricted to Spandex, and other mechanisms of closure. The closure device (34) can be used with solids and gels to include but not restricted to Velcro, adhesive tape, rope, bands, cloth to include but not restricted to Spandex and other materials to include but not restricted to fabrics, rubber and latex materials, paper and other natural and synthetic materials.

Figure 11A:
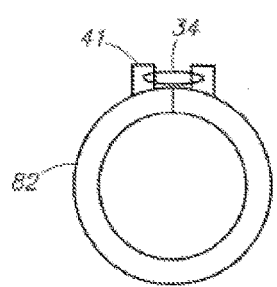
FIG. 11A depicts a closure device that is fully circumferential.

In FIG. 11A, the closure device (34) can be attached to a structure that is fully circumferential or annular (82) and there is no increased pressure exerted by the closure device (34).

Figure 11B:
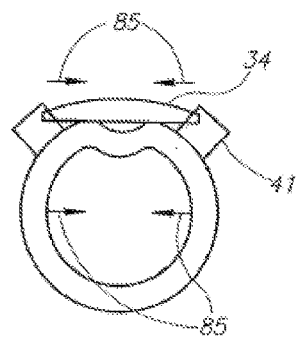
FIG. 11B, depicts a closure device that is be fully circumferential and there is increased tension and pressure exerted by the closure device.

In FIG. 11B, the closure device (34) can be fully circumferential (82) and there is increased tension and pressure exerted by the closure device (34). This can be used to increased pressure (85) on the enclosed organ that can include but is not restricted to use for the penis for treatment of erectile dysfunction; stop bleeding of a battlefield wound by controlling arterial and venous pressure; insuring a secure attachment of a device based on how vigorous of an activity is being undertaken when a device is attached to the user; and creating a stepwise closure of a wound. By varying one or all of the elements of closure and the closure device (34) to include but not restricted to elasticity, length and multiplicity of the closure elements (34) and varying the location, elasticity, length and multiplicity of the closure attachment (41), the tension and pressure can be customized to uniquely fit each user and each application.

Figure 12A:
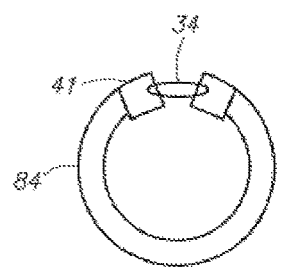
FIG. 12A depicts a closure device that is partially circumferential.

In FIG. 12A the closure device (34) can be partially circumferential (84).

Figure 12B:
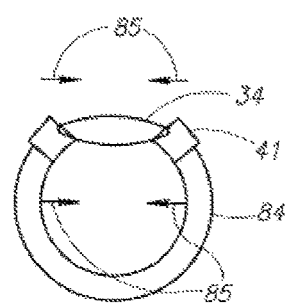
FIG. 12B, depicts a closure device that is partially circumferential and there is increased tension and pressure exerted by the closure device.

In FIG. 12B, the closure device (34) can be less than fully circumferential (84) and there is increased tension and pressure (85) exerted by the closure device (34). This can be used to exert increased pressure (85) on the enclosed organ that can include but is not restricted to use for the penis for treatment of erectile dysfunction; stop bleeding of a battlefield wound by controlling arterial and venous pressure; insuring a secure attachment of a device based on how vigorous of an activity is being undertaken when a device is attached to the user; and creating a stepwise closure of a wound. By varying one or all of the elements of closure and the closure device (34) to include but not restricted to elasticity, length and multiplicity of the closure elements (34) and varying the location, elasticity, length and multiplicity of the closure attachment (41), the tension and pressure can be customized to uniquely fit each user and each application.

Figure 13:
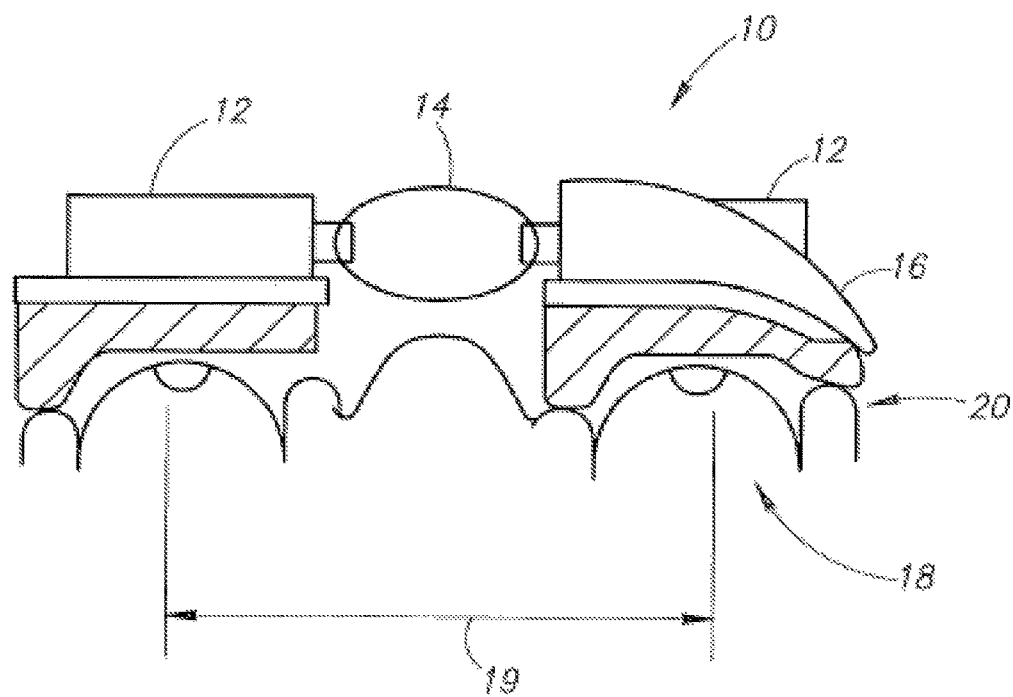
FIG. 13 is a method and a device for varying the shape of the seal, goggle or a combination of seal and goggle to conform to the user's orbit.

FIG. 13 is a method and a device for varying the shape of the seal (16) to conform to the users orbit. This variation creates variable thickness of the seal (16). In the preferred embodiment the seal (16) would be made of gel and would be thinner closer to the nose and thicker away from the nose at the lateral margin of the orbit. This invention allows the variable and flexible seal (16) to serve as a conforming element of the goggle (10) to the human orbit, which is curved and varies with the variations that are present in humans of varying facial (20) shapes. Variations in the seal (16) and variations in the nosepiece (14) and the eyepiece (12) can all be adjusted to create a more unique fit for the user to include but not restricted to an adjustment to facial contours (20) and eye and orbital socket (18) and interpapillary distance (19). Other materials can be used of variable thickness to conform to the orbit to include but not restricted to foam and silicon and other non-gelatinous elastomers.

Figure 14:
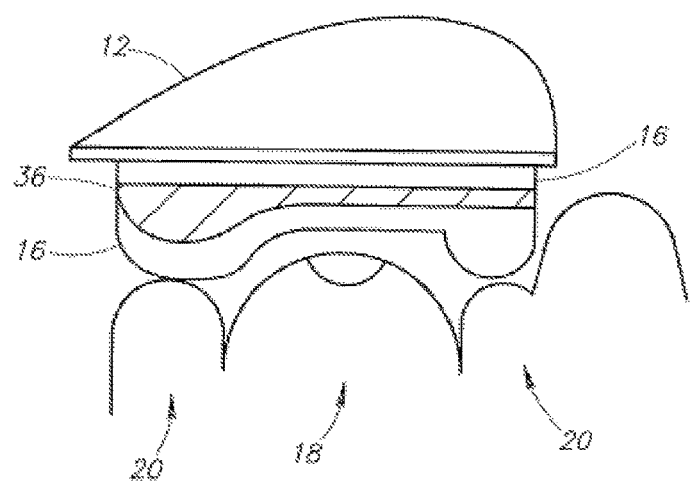
FIG. 14 depicts a flex Layer in which there is a transitional layer within or between the airtight or watertight sealing between a rigid or semi-rigid or flexible frame and the sealing pad.

FIG. 14 is a FLEX Layer (36) which a transitional layer (16) within or between a rigid or semi-rigid or flexible frame (12) and the airtight or watertight sealing pad (16). The FLEX layer (36) will adjust to the shape of the orbit 18 and facial contour (20). The flex layer (36) is composed of a material that is resiliently deformable and can expand or contract to the users face in a manner that differs from the sealing layer (16) and the frame, eyepiece (12). The Flex (36) layer has characteristics that differ from the frame, eyepiece (12) and the sealing pad (16). The sealing pad (16) can be airtight or watertight or it can be partially airtight or watertight or it can be non-airtight or non-watertight. In the preferred embodiment the sealing pad (16) is composed of a resiliently deformable gel elastomer. The flex layer can be composed of a solid, gel, liquid or gas or a combination of a solid, gel, liquid or gas. The FLEX layer (36) can be composed of one or multiple layers.

Figure 15:
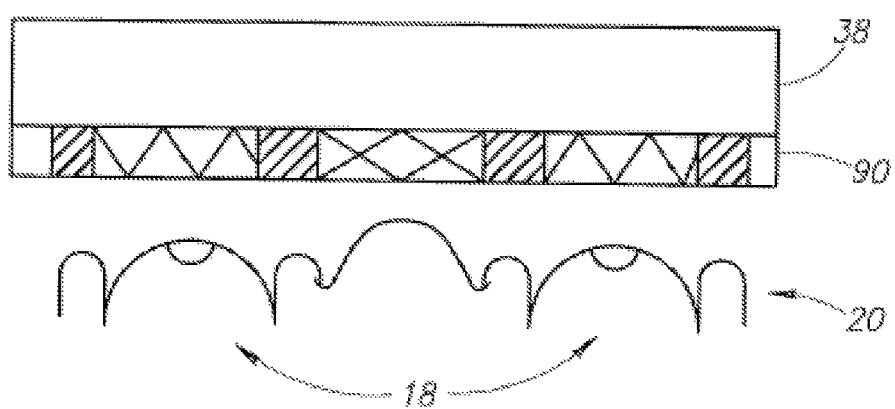
FIG. 15 depicts a testing device used to assist a user when selecting and purchasing a goggle that uses a gel that covers the orbits and that is pressure sensitive and that changes color to display the degree of pressure and thickness required to create and airtight and watertight seal.

FIG. 15 is a testing device (38) to assist the user who is the purchaser in choosing the 'best fitting' goggles. The invention in the preferred embodiment uses a gel that covers the orbits (18) and Face (20) that is pressure sensitive and that changes pattern or color (90) to display the degree of pressure and thickness required to create and airtight and watertight seal. When pressed against the orbit (18) and face (20) the gel will register the change in color by changing color at the pressure points. In one embodiment the color displayed on the gel tester can then be compared to a color code that is printed on packaging. The purchaser can then more reliably find a pair goggles 10) that will likely conform to their face to form an airtight and watertight seal. This invention can be used for other fit or form applications.

In FIG. 15, the testing device (38) can utilize one or multiple physical characteristics to assess and determine 'best-fitting goggles'. Some physical elements can include but are not restricted to pressure, heat, and the electromagnetic energy to include but is not restricted to infrared and ultraviolet and thermography and ultrasound. In one embodiment, the tester can be physically placed against the orbit (18) and pressure or heat can be used to sense the shape of the orbit (18) and the 'best-fit' seal (16) and goggle frame or a combination of seal (16) and goggle frame. The topographic analysis of the face contours is then fed into a computer.

Figure 16:
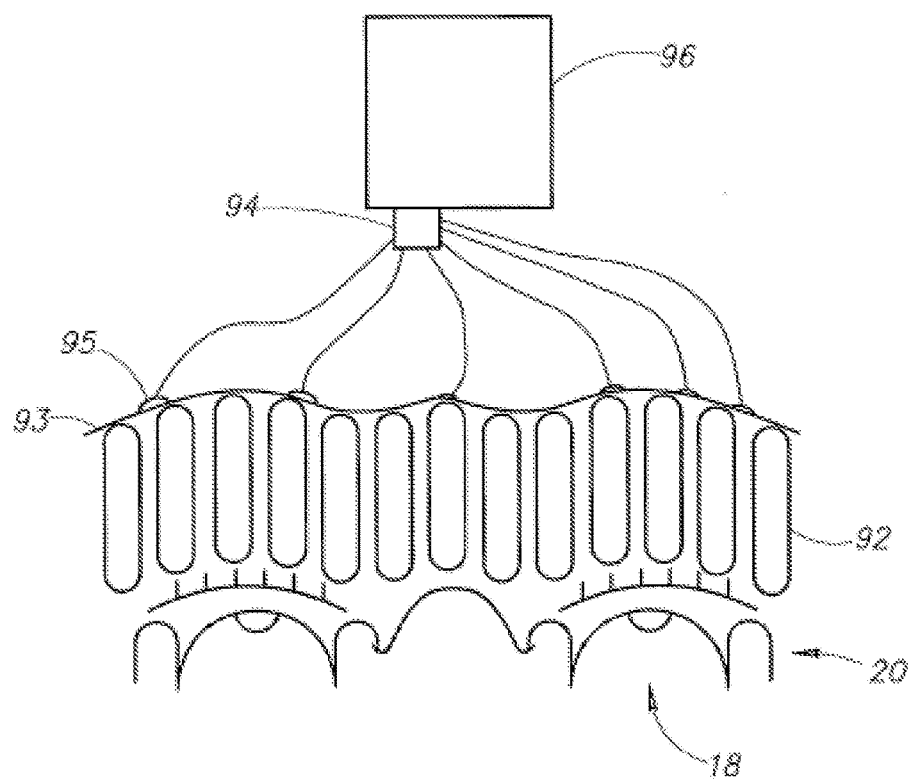
In FIG. 16 depicts a testing device that can use a mechanical device that to assess 3-D facial topography, biometrics, that when the face is pressed against the mechanical device which can include but is not restricted to the use of pegs that are displaced when pressed against the face.

In FIG. 16, the testing device (38) can use a mechanical device that to assess 3-D facial topography, biometrics, that when the face is pressed against the mechanical device which can include but is not restricted to the use of mechanical elements, similar to a Pin Toy made by Blip that are displaced when pressed against the face (20). In the preferred embodiment the displacement of the mechanical pegs (92) creates an impression of the face (20), which can remain as an analog image that can be utilize to assess the best-fitting goggles for the user or can be altered to form an analog image (93) and the analog image can be transformed through receptors and transmitters (95) that can include but are not restricted to wires and a wireless method and transmitted into a digital image (94) that can be entered into a computer (96) that can assess the best-fitting goggles for the user. In another embodiment the digital image can be formed directly form the displacement of the mechanical elements (92) that can assess the best-fitting goggles for the user. Any combination of the analog and non-analog imaging can be utilized to assess the best-fitting goggles for the user.

Figure 17:
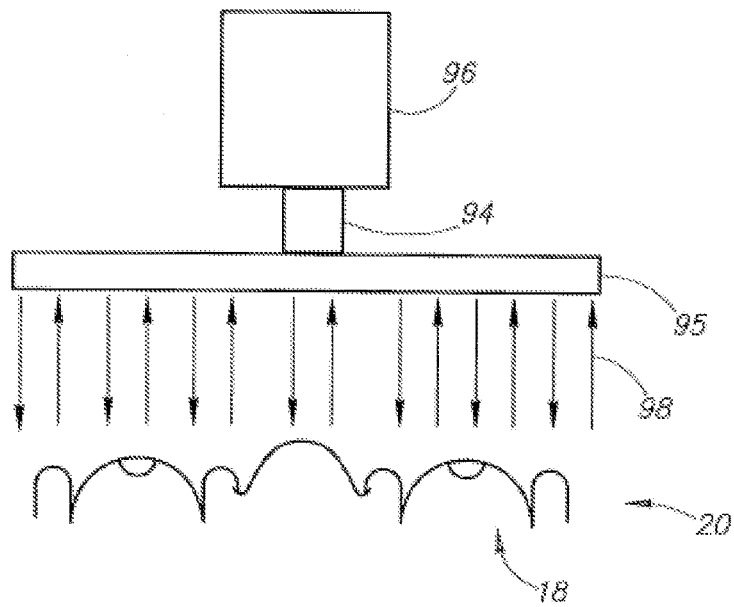
In FIG. 17, the testing device can use ultrasound to assess 3-D facial topography, biometrics.

In FIG. 17, the testing device (38) can use ultrasound (98) to assess 3-D facial topography, biometrics.

Figure 18:
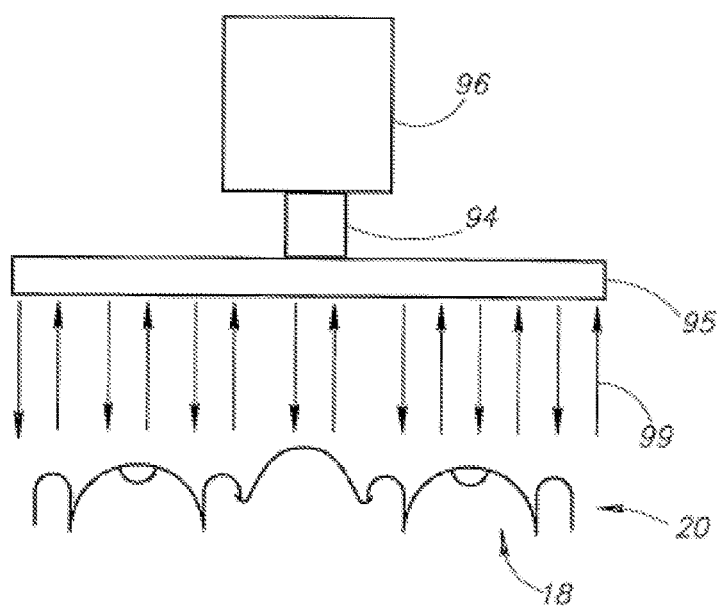
In FIG. 18, the testing device can use light or lasers to assess 3-D facial topography, biometrics.

In FIG. 18, the testing device (38) can use light or lasers (99) to assess 3-D facial topography, biometrics.

Figure 19A:
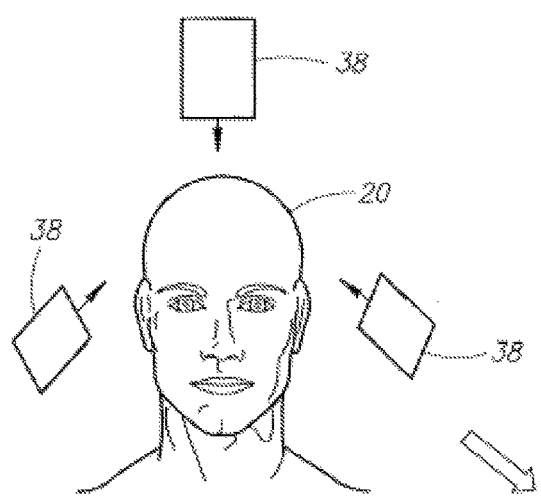
FIGS. 19A-C present a testing device that can consist of a 3-D topographic set up using cameras and lasers where there can be stationary units and the fitting device can be used to create a seal that can be airtight or watertight or an acoustic seal that conforms to the user's face/body part. And in one embodiment can be associated with a goggle or eyepiece.

FIG. 19A is a testing device 38 that can consist of a 3-D topographic set up using cameras and lasers where there can be stationary units and the fitting device 38 can be used to create a seal 16 that can be airtight or watertight or an acoustic seal 16 that conforms to the user's face/body part 20. And in one embodiment can be associated with a goggle 10 or eyepiece 12.

Figure 19C:
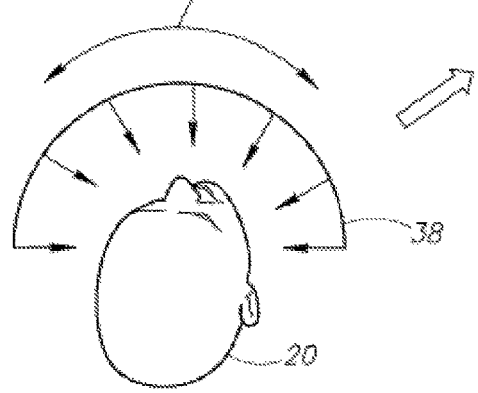
Figure 19B:
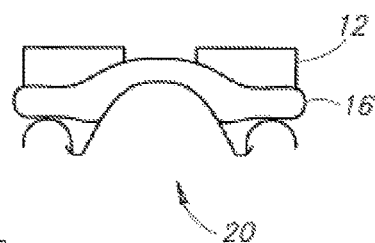

In FIG. 19B, the user's face/body part 20 is initially stationary and the imaging devices 38 are placed in strategic positions around the users face/body part 20. In this embodiment, the user's face/body part 20 can rotate or move 100 relative to the cameras or imaging devices 38. There can be one or more than one imaging device 38. The imaging devices 38 can include but are not restricted to cameras that utilize electromagnetic Energy such as visible light. In another embodiment the imaging device can include kinetic Energy or vibrational or ultrasound imaging devices or combination of electromagnetic and mechanical and vibrational and kinetic energy.

In FIG. 19C, the user's face/body part 20 is stationary and the imaging device 38 can rotate or move 100 relative to the user's face/body part 20. In another embodiment the user's face/body part 20 is stationary and imaging device 38 can have components that allow the energy propagation to begin at one position and rotate or move 100 to a different position.

Figure 20A:
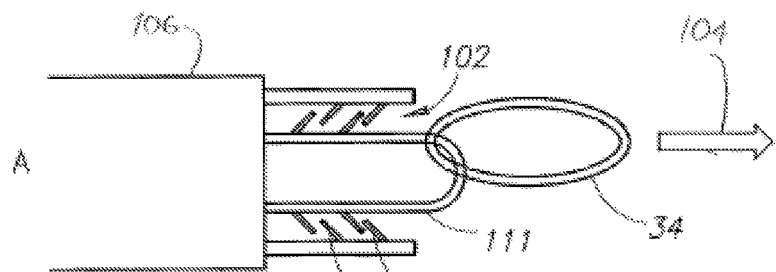
FIG. 20A is a material with primary attachment device in which a secondary attachment device can be inserted and held in place by flanges or bristles or outcroppings in the presence of a force upon the secondary testing device.

FIG. 20A is a material with primary attachment device 11 in which a secondary attachment device 111 can be inserted and held in place by flanges 102 or bristles 102 or outcroppings 102 in the presence of a force upon the secondary testing device.

Figure 20B:
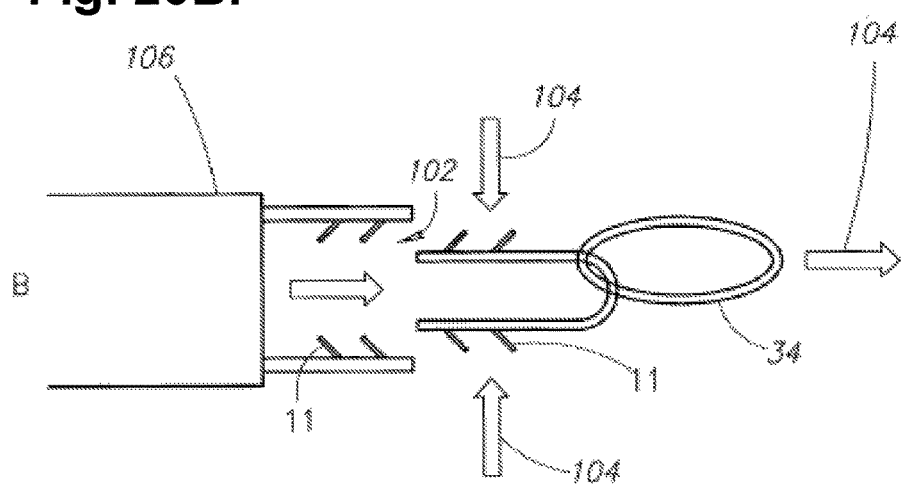
FIG. 20B is an embodiment in which the secondary attachment device can be removed from the hollow of the primary attachment device.

FIG. 20B is an embodiment in which the secondary attachment 111 device can be removed from the hollow of the primary attachment device 11.

FIG. 20A is the edge of a material 106 onto which there is an attachment device 11. This is primary attachment device has numerous flanges 102 or bristles 102 or outcroppings 102. The orientation of the outcroppings 102 were flanges 102 or bristles 102 is such that what a second attachment device 111 is placed into the hollow of the first attachment device 11 it can be restrained from moving out of the hollow of the first attachment device by a series of flanges 102 or bristles 102 or outcroppings 102 that are oriented in the same direction as the primary attachment device 11 hollow flanges 102 or bristles 102 or outcroppings 102. FIG. 20 A demonstrates this embodiment and demonstrates and an elastomeric strand 34 or band 34 or closure device 34 attached to the secondary attachment device 111. When a force 104 is placed away from the attachment device 11, 111 or strand 34 or band 34 or closure device 34 the strand 34 or band 34 or closure device 34 can stretch but the secondary attachment device 111 remains fixed within the first or primary attachment device 11.

FIG. 20B is an illustration that show secondary attachment device 111 being removed from the primary attachment device 11 by squeezing or putting pressure force 104 one the secondary attachment device 111 such that the distance between the components of the secondary attaching device 111 are narrowed and the bristles 102 were outcroppings 102 or flanges 102 can be removed from the hollow of the primary task device.

Figure 21A:
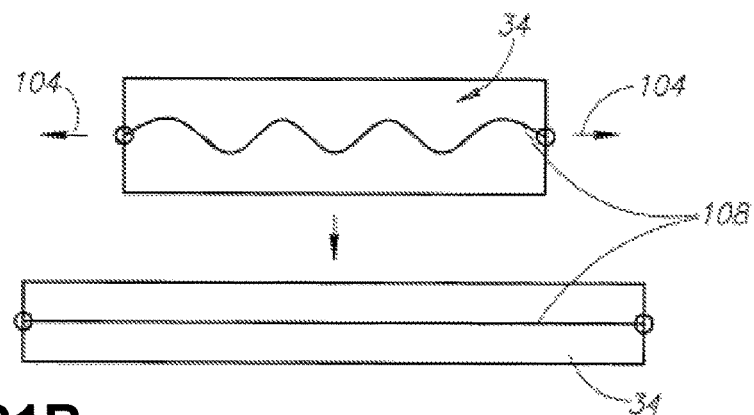
FIGS. 21A and 21B show another embodiment in which a strand or band or closure device is composed of an elastic material with a governing material embedded within the elastic strand or band or closure device that limits where governs the length of the specific individual strand.
Figure 21B:
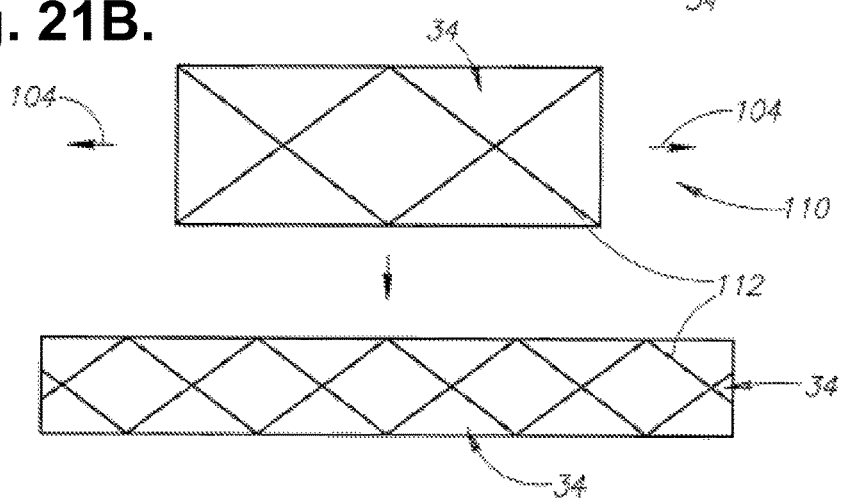

FIGS. 21A and 21B show another embodiment in which a strand 34 or band 34 or closure device 34 is composed of an elastic material with a governing material 108 embedded within the elastic strand 34 or band 34 or closure device 34 that limits where governs the length of the specific individual strand.

In FIG. 21A, a metallic wire 108 is embedded within the elastic strand. The wire 108 can be undulating or coiled and as the elastic strand expands the wire will limit or govern the maximal stretch of the strand 34 or band 34 or closure device 34 in the x axis but will not alter the movement in the y axis or the z axis or both the y and z axes when subjected to a force 104 which can include but is not restricted to a distraction or a pulling or pushing force 104.

In FIG. 21B, a composite material 112 that is embedded within the elastic strand 34 or band 34 or closure device 34 and the composite material has a geometric shape that will limit the strand 34 or band 34 or closure device 34 in one or more than one of its axes when subjected to a force 104 which can include but is not restricted to a distraction or a pulling or pushing force 104.

Figure 22A:
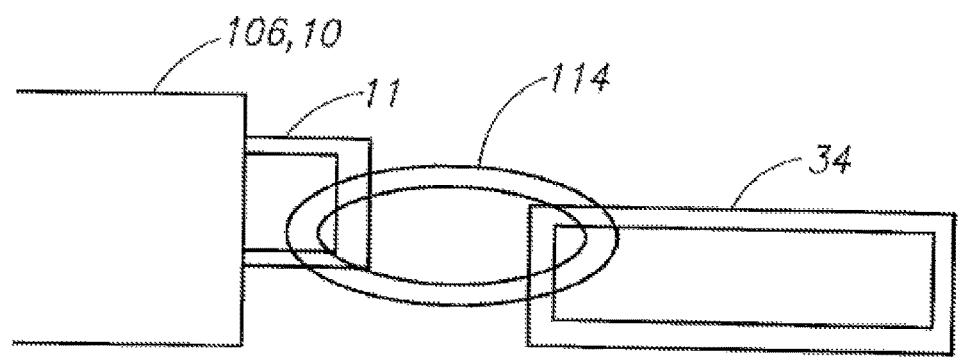
FIGS. 22A-C are representations of an embodiment a kit in which there can be a coupling device such that the embodiments of the elastic strand or band or closure device nosepiece herein can be used with goggles made from different manufacturers.

FIGS. 22A, B and C are representations of an embodiment a kit in which there can be a coupling device 114 such that the embodiments of the elastic strand 34 or band 34 or closure device 34 nosepiece 14 herein can be used with goggles 10 made from different manufacturers.

FIG. 22A is a representation in which the attachment piece 11 is annular and elastomeric strand 34 or band 34 or closure device 34 is fitted into the annular attachment piece using a coupling device 114.

Figure 22B:
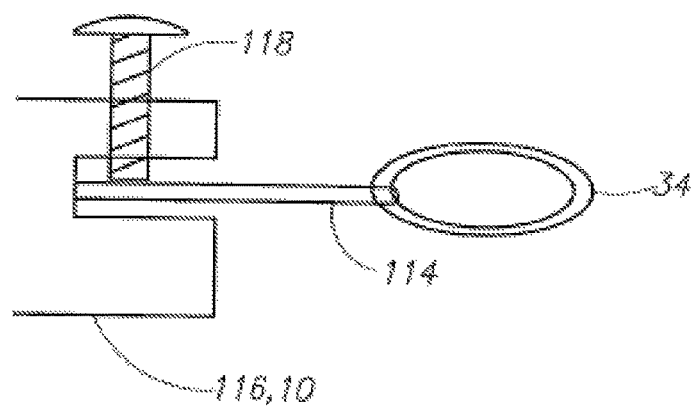

FIG. 22B is a representation in which the attachment piece 11 is slotted and contains a screw 118 and a flat coupling device 114 that is compressed against the wall of the slotted attachment piece 11 and the elastic strand 34 or band 34 or closure device 34 is attached to the flat transitional coupling device 114.

Figure 22C:
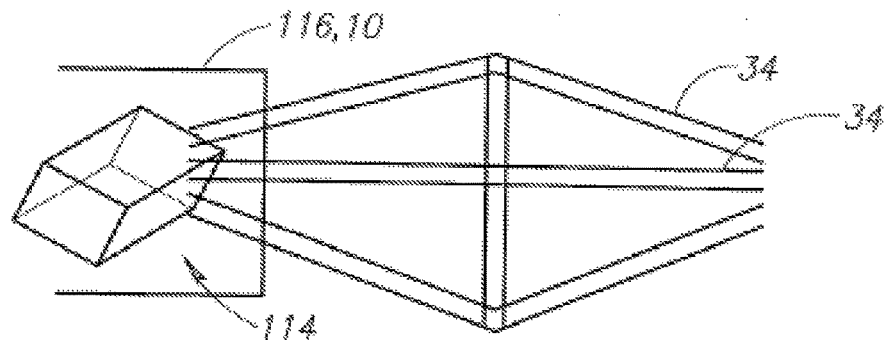

FIG. 22C is a representation in which a solid key coupling device 114 is placed into a hole in the attachment piece 11 and multiple of elastic strand 34 or band 34 or closure device 34 are attached to the coupling device 114.

Figure 23:
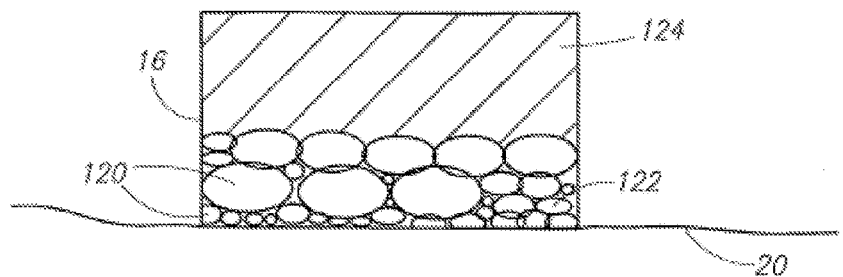
FIG. 23 is a seal or sealing pad or gasket in which a component of the seal or sealing pad or gasket can be composed of a phase change material (PCM) or a phase change slurry (PCS) that can be composed of encapsulated on non-encapsulated PCM or PCS material to create an airtight or watertight or acoustic seal with the users skin/face or body part and can be incorporated into another material that can include a solid, liquid or gel or gas that can if needed compose a portion of the seal.

FIG. 23 is a seal 16 or sealing pad 16 or gasket 16 in which a component of the seal 16 or sealing pad 16 or gasket 16 can be composed of a phase change material (PCM) 120 or a phase change slurry (PCS) 122 that can be composed of encapsulated on non-encapsulated PCM 120 or PCS 122 material to create an airtight or watertight or acoustic seal 16 with the users skin/face 20 or body part 20 and can be incorporated into another material 124 that can include a solid, liquid or gel or gas that can if needed compose a portion of the seal 16.

FIGS. 24A-G are representations of multiple strand 34 or band 34 or closure device 34.

Figure 24A:
FIGS. 24A-G are representations of multiple strand or band or closure device.
Figure 24B:
Figure 24C:
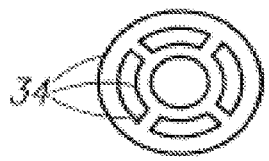
Figure 24D:
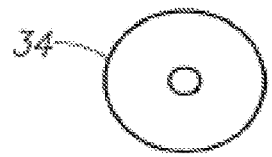
Figure 24E:
Figure 24F:
Figure 24G:
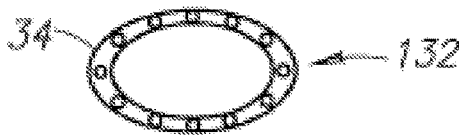

FIGS. 24A-C, illustrate that the strand 34 or band 34 or closure device 34 can be of different sizes thicknesses and shapes.

In FIGS. 24D-G, the strand 34 or band 34 or closure device 34 can have different elastomeric qualities of the strand 34 or band 34 or closure device 34 and each can have a recognizable method and means of designating the different elastomeric bands which can include but is not restricted to color or texture or shape. In this example the bands are designated as different colors red 130 green 131 and blue 132.

Figure 25A:
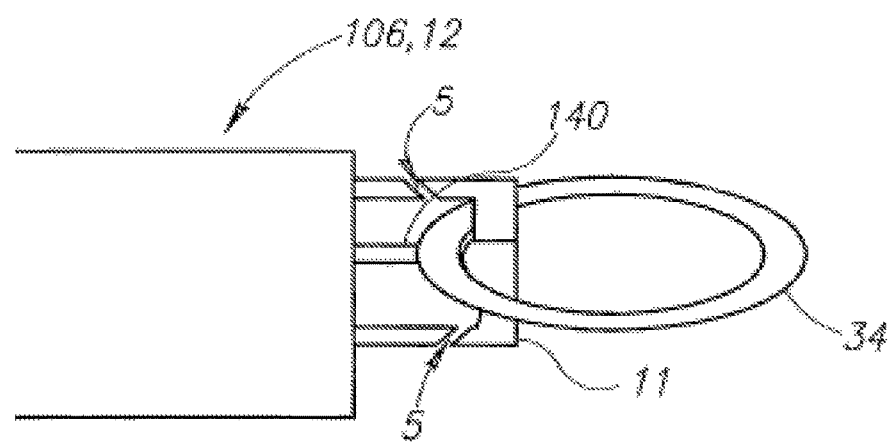
FIGS. 25A and 25B are representations of different methods for constructing the attachment component to the eyepiece or the object to be closed or bridged.
Figure 25B:
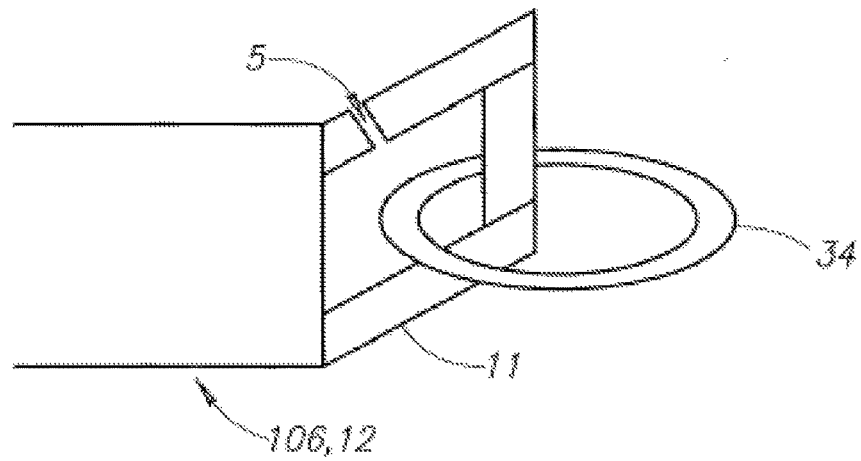

FIGS. 25A and 25B are representations of different methods for constructing the attachment component 11 to the eyepiece 12 or the object 106 to be closed or bridged.

In FIG. 25A, the attachment device 11 can contain one or more partitions 140. The partitions 140 can also include one or more slits 5 for allowing the elastic strand 34 or band 34 or closure device 34 to fit into the attachment piece 11 104 partitions.

In FIG. 25B, the attachment device 11 can be angled to allow for a better fit or contour particularly near a body part structure 20 that protrudes, such as the nose.

FIGS. 26A-D are representations of a nosepiece 14 or eyepiece 12 or strap 26 or an elastic strand 34 or band 34 or closure device 34 that can incorporate a swivel or ball bearing like rotational/movement element 142 that can move 150 in a manner to include but not restricted to swivel or rotate or move in an angular or curvilinear or spiral manner and can adjust to the energetic forces 104 to include but not restricted to compression or pressures to adjust to the user's contours of the face/skin/body parts 20.

Figure 26A:
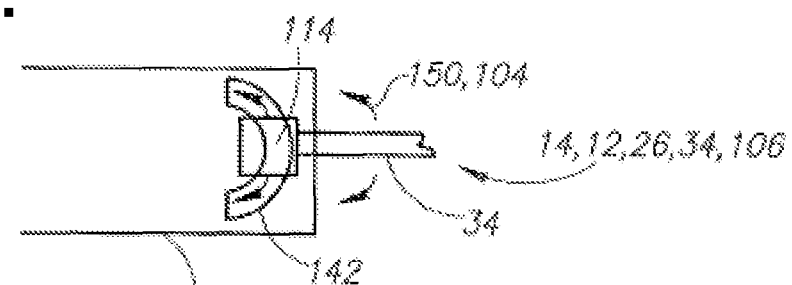
FIGS. 26A-D are representations of a nosepiece or eyepiece or strap or an elastic strand or band or closure device that can incorporate a swivel or ball bearing like rotational/movement element that can move in a manner to include but not restricted to swivel or rotate or move in an angular or curvilinear or spiral manner and can adjust to the energetic forces to include but not restricted to compression or pressures to adjust to the user's contours of the face/skin/body parts.

FIG. 26A depicts the movement element 142 that can be a slot 142 incorporated into the attachment device 11 in which a coupling device 114 is attached to the elastomeric strand 34 or band 34 or closure device 34 and which can be continuous and can be fitted into the slot 142. The coupling device 142 and the attachment device 11 can then move freely relatively to each other within the slot 142 and assist the strand 34 or band 34 or closure device 34 to conform to the user's body contour 20 or ergonomics 152 and movements 150 and forces 104.

Figure 26B:
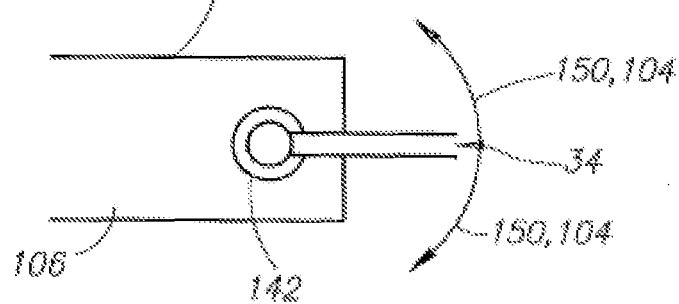

FIG. 26B is a representation of an attachment device 11 with an elastic strand 34 or band 34 or closure device 34 that fits into a circular movement device 142 within the attachment device 11 of the object 106 being bridged or closed or connected.

Figure 26C:
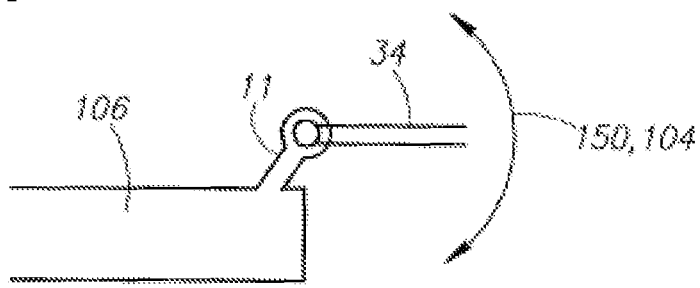

FIG. 26C is an attachment device 11 that is angulated and has a single movement point of motion 150, 104 relative to the attachment device 11 and elastic strand 34 or band 34 or closure device 34.

Figure 26D:
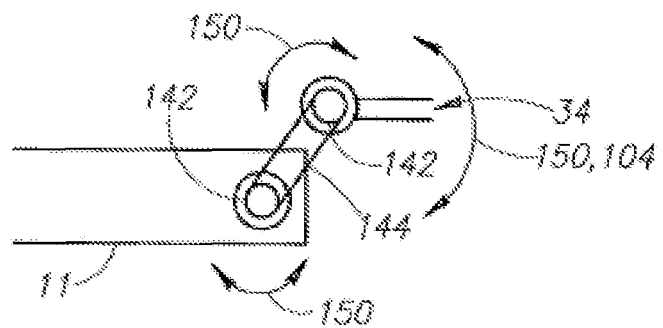

FIG. 26D is a test of device that has more than a single movement point 142 in response to motion 104, 150 relative to the attachment device 11 and the elastic strand 34 or band 34 or closure device 34 And can incorporate one or more than one coupling devices 144 to facilitate the motion 104,150.

Figure 27:
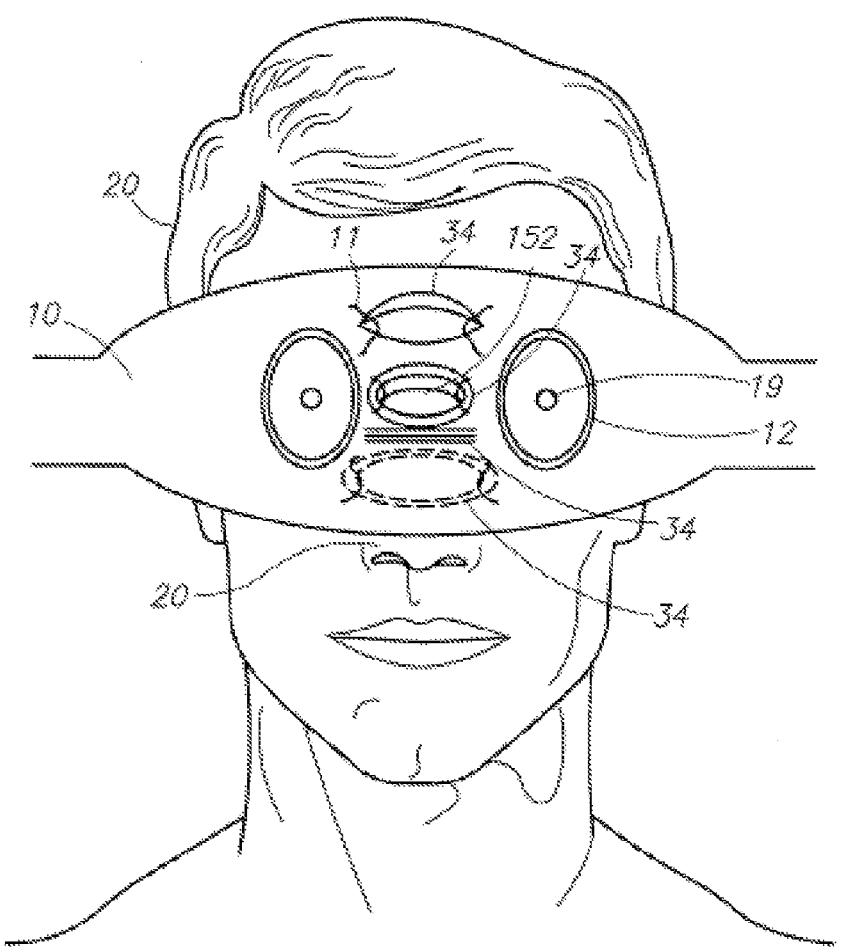
FIG. 27 is a representation of a uni-body mask/goggle in which the region of the nosepiece can be adjusted relative to the eyepieces and the pupils. In this embodiment the mask or goggle can be flexible and can be made out of a soft stretchable material that can include spandex or a cloth like material. In this uni-body mask or goggle the central region of the mask or goggle that corresponds to the region between the eyepieces, the region of the nose, can contain elastomeric materials that can stretch and flex and adjust to the users inter-pupillary distance and contours of the users face.

FIG. 27 is a representation of a uni-body mask/goggle 10 in which the region of the nosepiece 14 can be adjusted relative to the eyepieces 12 and the pupils 19. In this embodiment the mask or goggle 10 can be flexible and can be made out of a soft stretchable material that can include spandex or a cloth like material. In this uni-body mask or goggle 10 the central region of the mask or goggle 10 that corresponds to the region between the eyepieces 12, the region of the nose 20, can contain elastomeric materials 34 that can stretch and flex and adjust to the users interpupillary 19 distance and contours of the users face 20. FIG. 27 demonstrates three embodiments. The first embodiment includes an area that is cut out 152 of the mask/goggle 10 that can contain the elastomeric strand 34 or band 34 or closure device 34 and attachment devices 11. In another embodiment the attachment device 11 and strand 34 or band 34 or closure device 34 can be on the surface of the mask or goggle 10 on the side opposite of the users skin/face 20. In another embodiment the attachment device 11 and elastic strand 34 or band 34 or closure device 34 can lie on the surface of the mask/goggle 10 on the side between uses face 20 and the mask/goggle 10. In another embodiment the elastic strand 34 or band 34 or closure device 34 can be embedded or incorporated into the mask or goggle 10.

Figure 28A:
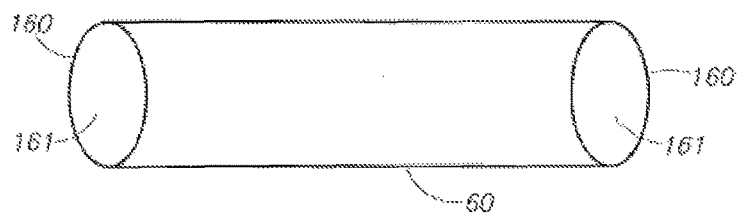
FIGS. 28A-C are representations of a method that can create a cast cover, which uses physical measurements or a topographical 3-D device to determine the optimal size and shape and configuration of a covering device. In this embodiment, the covering device is a cast cover.
Figure 28B:
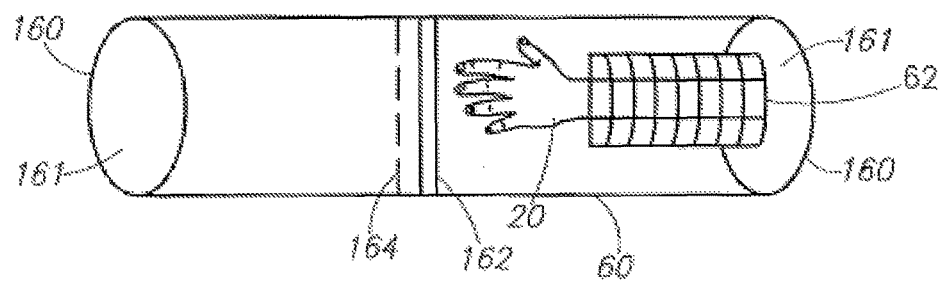
Figure 28C:
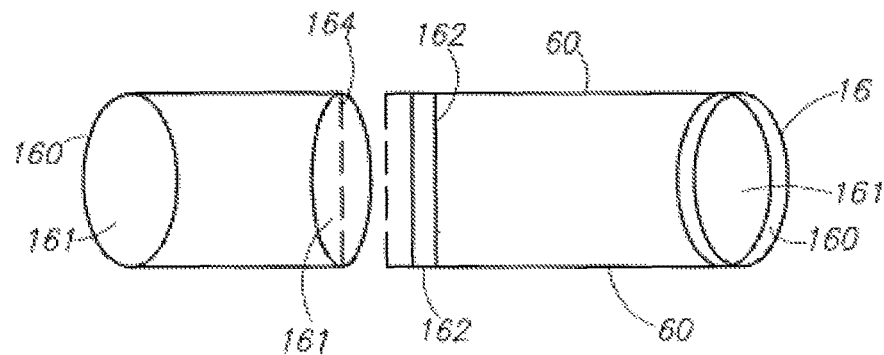

FIGS. 28A-C are representations of a method that can create a cast cover 60, which uses physical measurements or a topographical 3-D device to determine the optimal size and shape and configuration of a covering device 3, 60. In this embodiment the covering device is a cast cover 60.

FIG. 28A demonstrates a plastic belong gated hollow tube 160. This tube can be located and wound on his spool (not shown).

FIGS. 28B and 28C demonstrate the cast cover 60 and an arm/body part 20 and cast 62 length that is calculated by a measuring device. Using the image or size and proportions measurements the proper length of the hollow tubing 160 can be determined. Once the length of tubing is designated a portion or all of the tube can be sealed 162 creating a watertight end of an open hollow tube 160 that was previously open 161 at both ends. Now the tube 160 is closed and watertight fused or closed 162 at one end and open 161 at the other end. This will allow the hand cast to pass through the open-end 161 and the tube will be precisely the correct length required to cover the cast 62 and the body part 20 with an airtight and watertight seal 16 with the skin 20 (not shown) and the fused or close 162 end that is now airtight and watertight. The dotted line represents the site where the tube that is still attached to the role can be cut and a new opening 161 exists that will allow for a new cast cover 60 to be created.

FIG. 28C demonstrates the final product with a cast cover with its airtight and watertight seal in place 16, which is at the optimal length for the cast cover 60 and the hollow tube 160 is ready for creating another cast cover 60 segment.

Current static closures put the stress on the object being closed and not on the closure device. In this invention the closure device adjusts and absorbs the burden of movement.

In goggles with an independent eyepiece, the nosepieces demonstrate little to no elasticity or flexibility or ability to stretch. There is a goggle uni-body, one piece goggle in which the entire goggle is made of a more flexible material and this goggle is made by AquaSphere, Inc, (see Aqua Sphere Kaiman Goggle Smoke Lens) Despite the fact that this nosepiece is more elastic, it is not adjustable and the eyepiece frame is not rigid. The pre-determined length and stretch of the manufacturer limits the nosepiece and goggle.

In this specification, the user can choose from a series of bands or strands that can have different lengths and/or can have different abilities to stretch and/or can have different elasticity and/or can have variable elasticity within the bands or strands and/or any combination of these element. In turn, the user can select from the multiple bands or strands. The user can then select from these multiple bands or strands to create the optimal fit for the users face/skin or contours of the body. The choices of multiple strands, allows the user to adjust the eyepieces of the goggles and/or seal to fit the specific and particular unique features user's face/skin or contours of the body and to create a best-fit goggle and seal. By using one or more than one band or strand the user can adjust the goggle seal to fit the user's face by adjusting the ability of the nosepiece to stretch and flex. This stretching and this flexibility can occur in three different axes. Using one or more than one band or strand of differing lengths and differing elasticity and differing and variable stretching ability and variable flexibility, the nosepiece effectively takes on a continuous elasticity and flexibility and ability to stretch. As a result the user can choose from one or more than one band to find the best fit seal based on the stretch for flexibility or elasticity that proves most effective for that particular user to create the most effective seal and best-fit goggle. "The plethora of possible adjustments to the nosepiece described above results, for all practical purposes, in the amount of stretch of the nosepiece being continuously adjustable by the user."

The nosepiece can have variable elasticity either by using one strand that has a variable amount of elasticity built into one portion of that strand or band. In one embodiment to include but not restricted to a strand or band being more elastic in the lateral position/near the eyepieces than the region that is centrally located within the band or strand and positioned between the eyepieces. In one embodiment the nosepiece can be made more variable by using materials that are more elastic at the margins of the strand or band. In another embodiment the elasticity can be variable by altering the thickness of the strand or band. In another embodiment the elasticity can be variable by altering the geometric shape or configuration of the strand or band. In another embodiment multiple strands for bands can be used to alter the variable elasticity of nosepiece. In this embodiment the nosepiece variable elasticity can include but is not restricted to having one or more than one additional bands or strands which are composed in the manner in which that or those particular strands or bands can have different elasticity, what thickness, or laying than other bands or strands.

In current goggles with independent eyepieces there is little to no ability for the user to adjust the nosepiece or eyepiece in the X-axis or horizontal plane. There is also little to no ability for the nosepiece or eyepieces of the goggles to adjust in the other Y and Z axes, the anterior-posterior and cranial-caudal axis, respectively. When the head-strap places pressure and stretch on the goggles relative to the face/skin the current nosepieces provide little to no ability of the eyepieces to move independently and adjust to the facial contours and asymmetries. Since the vast majority of humans have asymmetric face/skins, and asymmetric and variable contours to their facial profile and orbital depth and cheek prominence and zygomatic prominence, it would be beneficial if the eyepieces had the ability to move independent of each other in all three axes. This would improve the watertight fit and would reduce the pressure of the goggle seal on the skin. By creating a nosepiece that can move and adjust in all three planes the goggle seal and the comfort of the goggle on the users face/skin can be improved simultaneously. The current embodiment nosepiece invention serves this need.

Although there are one-piece uni-body, one piece, continuous eyepiece and nosepiece goggles which can include one-piece straps that are flexible these goggles and the flexibility of the unit are pre-determined by the manufacturer and have a fixed or a fixed or limited range of pre-determined specifications. The goggle's ability to adjust to the user is evident by studies that show the typical goggle is truly comfortable and watertight in only 50 to 60% of users because of the limited range of adjustments and movements of the goggle eyepieces and nosepieces and straps provided by any individual the goggle maker and the specific goggle specifications manufactured and purchased.

The independent Dynamic 3-Axis Motion Nosepiece and Connector allows a new broader range and latitude of flexibility and adaptability of the goggle seals for the eyepieces. It allows for new designs in the seal that can adjust more comfortably and effectively to each user's face/skin. Some examples include but are not restricted to an example if a user has a pair of goggles that leaks on the outside current goggles require the strap to be drawn tighter so that more compressive force is generated by the goggle against the face/skin. This pressure generated to seal the outside of the goggle forces greater pressure onto areas that are already tightly sealed and this can lead to user discomfort or damage to the delicate thin skin and the delicate vessels that exist in the lower parts of the orbits or can place pressure on the orbits which can lead to unhealthy pressure on the delicate eye/globe and can lead to changes in intraocular pressure and damage to internal eye/globe structures and could lead to glaucoma or can lead to retinal detachment or can result in neurologic reflexes such as vagal responses when undo pressure is placed onto the eyeball/globe. In this example what is really needed is for the pressure that is already being generated to be better and more effectively and 'smartly' distributed. A betting fitting goggle can occur by simple by transferring the pressure to the proper location, which in this example is the outside edge of the goggle, the portion away from the nose. The concept of adjusting the fit by using the nosepiece as a variable in the fit and creating a better and more comfortable fit can be replace the current concept of creating a better fit by pressing the goggle against the face/skin tighter and tighter and generating more and more pressure which leads to greater discomfort and potential facial damage such as dark rings under the eyes of swimmers secondary to tissue and small vessel damage and even with this increased pressure the goggle may still leak because the pressure is not successfully generated in the needed location which in this example is the lateral margin or outer portion of the eyepiece seal and goggle. Other embodiments can include but are not restricted to redirecting compression/pressure to the inner/medial region, superior/cranial or inferior/caudal regions of the orbit or in any region of the 360 degree radius of the seal and user's the eye or body part.

In another embodiment, the connector or bridging or closure element can be used for purposes other than a nosepiece and can include but are not restricted to a to be used with swimming goggles, a cast cover, a wound cover, a PIC Line cover, a respiratory or breathing mask to include but not restricted to a CPAP mask, a positive or negative pressure breathing mask, an intubation device, a male or female urinary condom catheter, ear buds, earphones, nose plugs, ostomy, an anal plug or anal catheter, penile ring or erectile function device, eye patch, vascular tube or catheter, hollow viscous catheter or tube, a seal for a surgical field which can be used to but not restricted to keeping the keeping a surgical field of infection or tumor from extending beyond its field or clothing such as but not restricted to footwear or gloves.

In another embodiment the forces that are modulated can include forces other than the adjustment of compression or pressure and can include but are not restricted to closure of objects, tightening, and distraction or separation of objects. An embodiment can include but is not restricted to closing a gaping wound where primary closure is limited or strained or not possible or a cast cover where an annular gel seal can be tightened so that the gel is overlapping and the seal is airtight and watertight but can be adjusted to allow the proper arterial inflow and venous outflow and lymphatic drainage.

In another embodiment the mask or goggles can be designed such that the eyepieces and the nosepiece are a uni-body design but the nosepiece or the component between the eyepieces can be structured to allow for the insertion or incorporation of an adjustable section between the eyepieces that incorporates the embodiments of closure and connecting and nosepiece design described herein. In one embodiment the mask/goggle can have a region that includes an area of the nose and/or is near the nose or inter-pupillary region or between the orbital region and that area can have a cut out or bare area that incorporated the nosepiece or connector or bridging 3 axis motion embodiments of this invention or the embodiments of the invention can be incorporated into the goggle/mask uni-body design of the eyepiece or nosepiece or strap or any combination of components or in another embodiment they can be on the surface or superficial to the uni-body design and this can include being superimposed on the membrane or covering material over the skin/face.

In one embodiment, since each individual has unique facial features there is a need for each nosepiece to be capable of adjusting uniquely and specifically for that user. The multiple embodiments that include but are not restricted to the nosepiece having elasticity in all three axes, and a stretchability that can alter the inter-pupillary distance, and a flexibility that can move with facial muscular movements and a malleability to assist the eyepieces to conformation to contours and structures of the face/skin. In addition the nosepiece can have a governor that can gradually or suddenly limit the movement, rotation, twisting, elasticity, stretchability, malleability of the nosepiece such that these features are not unlimited but rather are limited in their maximum and minimum properties. In addition these properties can be can have a linear or a non-linear response to forces that can include but are not restricted to forces to include but not restricted to pushing or pulling or compressing or lifting and that induce responses that can include but are not restricted to movement, rotation, twisting, elasticity, stretchability, and malleability, the current nosepiece invention has these properties.

In one embodiment, to create these responses and the governing of these responses and properties the nosepiece can be formed from one or more than one strand of material and each strand can have the same or different properties.

In one embodiment, the individual nosepiece strands properties can be fixed or they can be different or they can be variable or a mixture of these properties.

In another embodiment the nosepiece strands properties can have the same or a different initial property if there are multiple stands.

An another embodiment of having the same property can include but is not restricted to all of the strands being annular, all of the strands being non-annular, strands that are all the same circumference or length, all of the strands having the same response to forces that can include but are not restricted to pushing or pulling or compressing or lifting and that induce responses that can include but are not restricted to movement, rotation, twisting, elasticity, stretchability, and malleability.

An another embodiment of having different properties can include but is not restricted to some but not all of the strands being annular, being non-annular, strands that have all or less than all of the strands being different circumferences or lengths, or all or less than all of the strands having different responses to forces that can include but are not restricted to pushing or pulling or compressing or lifting and that induce responses that can include but are not restricted to movement, rotation, twisting, elasticity, stretchability, and malleability.

An another embodiment of having variable properties can include but is not restricted to one or more than one strand having and initial elasticity and a it is stretched the elasticity can increase or decrease, in responses to forces that can include but are not restricted to pushing or pulling or compressing or lifting. Other embodiments can include variable properties that can include but are not restricted to movement, rotation, twisting, elasticity, stretchability, and malleability.

In another embodiment the properties of the nosepiece can be altered with energies or forces that can include electromagnetic, chemical, Brownian, kinetic, and mechanical energies or forces.

In another embodiment the nosepiece can include one or be a combination of embodiments, such as but not restricted to multiple annular strands of different length but of the same elasticity, multiple strands of the same length but different elasticity.

In another embodiment a single or multiple strands can be composed as a composite or combination of one or more than one of the embodiment properties and example can include but is not restricted to a strand composed of an elastic material with a metallic wire embedded within the elastic strand. The wire can be undulating or coiled and as the elastic strand expands the wire will limit or govern the maximal stretch of the strand in the x axis but will not alter the movement in the y axis or the z axis or both the y and z axes.

In another embodiment a kit can be created for a universal coupling device such that the embodiments of the nosepiece herein can be used with goggles made from different manufacturers.

In one embodiment if the eyepiece has attachments that have an annular configuration can have a transitional component that can be annular or non-annular to include but not restricted to a compressible triangular shaped component that can fit through the inner diameter of the annular and then expand to become larger than the inner diameter and can attach the nosepiece to the transition piece and the eyepiece or can be an annular structure with a slit in the ring to allow it to attach to the annular component of the eyepiece or can be a flat strand that can have variable elasticity at a portion of the strand and can include but is not restricted to one portion of the strand and the some components can be harder, firmer, stiffer, or less elastic or stretchable and one or more other components can be less hard, firm, stiff or more elastic or stretchable and can fit into the various different eyepiece attachment designs. The transitional component can be attached to the nosepiece. The transitional component can compose one or more than one portion of the nosepiece.

In one embodiment the bridging material or nosepiece or connector can be directly attached to the seal or the frame or membrane relating to or attached to the seal and can change or dynamically alter the shape or the forces exerted on seal or frame and the relationship of the seal or frame to the face/skin.

In one embodiment a Keyhole can be created into the frame or seal or nosepiece/connector/bridge in order to interconnect and anchor these structures.

Because of the dynamic 3-axis movement of the nosepiece there is a movement of the eyepieces that occurs with this nosepiece that does not occur with the standard nosepieces. The forces on the eyepieces are altered. The compression force for the face/skin is distributed differently and in one embodiment the force can be translated such that a component of the downward compressive force is transferred to an outward force. Because of this alteration in the forces of the goggle and the goggle seal on the face/skin, the shape of the goggle and the goggle seal can be altered to create a more comfortable fit and some embodiments can include but re not restricted to curving the eyepiece to conform to the curvature of the face/skin, individualizing the curvature of the eyepiece, the seal or of both the eyepiece and the seal to conform to the face/skin, creating an asymmetric seal that is thicker in one or more portions of the seal than in other portions which can include but are not restricted to being thicker or have a variable hardness or softness or a combination of different thicknesses or hardness or softness qualities in the horizontal plane the vertical plane or the anterior posterior pane, which can include but is not restricted to positions near the nose than away from the nose, superior/cephalad than inferior caudal, or any combination of away from the nose than near the nose, or any combination of these axes. The seal can be created to be dynamic such that when a pressure is applied to the seal, the seal that pressure will result in a morphing of the thickness or plasticity or elasticity or hardness or softness the seal at the site of the presence or absence of the forces exerted. The seal or eyepiece can be composed of a transitional phase or phase change (PCM) material that can transition in its state of solid or gel or liquid or gas such that the properties of the seal or eyepiece alter when exposed to a substance to include but not restricted to a solid, a gel, a liquid such as but not restricted to water in the pool or a gas to include but not restricted to room air; or an energetic force that can include but are not restricted to heat, light, pressure, electromagnetic, kinetic, mechanical, vibrational, ultrasound or Brownian forces.

In another embodiment the seal or the nosepiece or the eyepiece or any combination of these components can have a portion of the component composed of a phase change material which can include but is not restricted to hydrophobic or hydrophilic materials or polymers or hydrates, fatty acids and esters, metals such as but not restricted to nitenol, paraffins such as but not restricted to octadecane or ionic liquids can be used to create an airtight or watertight or acoustic seal with the skin, or with a mucosal membrane to include but not restricted to the nasal cavity, the oral mucosa, the oral/digestive mucosa, the respiratory mucosa or with an orifice, the inner linings of the body such as but not restricted to the peritoneal lining, pleural lining, or the transitional space between the outer skin and the inner body to include but not restricted to the dermal, subdermal, subcutaneous, and cutaneous layers. For the purpose of this patent all of these linings and layers can be interchangeably referred to as skin or linings.

Phase change materials (PCM's) can include but are not restricted to encapsulated PCMs that are macro-encapsulations, micro-encapsulations and phase change slurries. This embodiment of phase change slurries as an added benefit can provide for the exchange of heat, which can be used to help prevent fogging of the eyepiece. A portion of the seal or the eyepiece or both can be composed of phase change materials and can be encapsulated or non-encapsulated or can be in the form of a slurry or not in the form of a slurry.

Another embodiment can include but is not restricted to a portion of the eyepiece that is composed of a phase change material that can include but are not restricted to encapsulated PCMs that are macro-encapsulations, micro-encapsulations or a phase change slurry.

Another embodiment can include but is not restricted to a portion of the nosepiece that is composed of a phase change material that can include but are not restricted to encapsulated PCMs that are macro-encapsulations, micro-encapsulations or a phase change slurry.

Another embodiment can include but is not restricted to a portion of the seal that is composed of a phase change material that can include but are not restricted to encapsulated PCMs that are macro-encapsulations, micro-encapsulations or a phase change slurry.

Another embodiment can include but is not restricted to a portion of the eyepiece, nosepiece or seal that is composed of a phase change material that can include but are not restricted to encapsulated PCMs that are macro-encapsulations, micro-encapsulations or a phase change slurry.

Another embodiment the use of transitional or phase change materials can be used as a seal that can include but is not restricted to swimming goggles and can be used with other seals that can include but are not restricted to a cast cover, a wound cover, a PIC Line cover, a respiratory or breathing mask, to include but not restricted to a CPAP mask, a positive or negative pressure breathing mask which can include and can be defined to include but is not restricted to surgical masks, protective masks; an intubation device, a male or female urinary condom catheter, ear buds, earphones, nose plugs, ostomy, an anal plug or anal catheter, penile ring or erectile function device, eye patch, vascular tube or catheter, hollow viscous catheter or tube, a seal for a surgical field which can be used to but not restricted to keeping the keeping a surgical field of infection or tumor from extending beyond its field, gloves, or clothing such as but not restricted to footwear or gloves.

In another embodiment the use of transitional or phase change materials can be used as a seal on can be used with other materials that can include but are not restricted to solids or liquids or gels or gases and the transitional or phase change materials can be placed within or superficially on the surface of said material or a combination of both. In one embodiment if the and if the transitional or phase change materials are placed superficially on the surface of said material then this can include laminating, coating, placing a covering membrane over said material and electrophoresis. In another embodiment the transitional or phase change materials can be embedded or intimately integrated into said material and in the preferred embodiment the transitional or phase change materials would be both integrated into and placed superficially in a laminar coating to adjust to the contours of the face/skin in not just a macroscopic but also in a sub-macroscopic or microscopic manner to insure an airtight or watertight or acoustic seal. In one embodiment said material can be a gel, or silicon based material or a plastic or polymer that can conform to the contours of the skin.

In one embodiment the nosepiece can be a kit that can include but not be restricted to nosepieces and transitional components that can form a Kit to use with goggles from different goggle makers.

Another embodiment the nosepiece can serve as a bridging or closure device to bridge or connect one or more than one structures and can include but are not restricted to a swimming goggles, a cast cover, a wound cover, a PIC Line cover, a respiratory or breathing mask to include but not restricted to a CPAP mask, a positive or negative pressure breathing mask, an intubation device, a male or female urinary condom catheter, ear buds, earphones, nose plugs, ostomy, an anal plug or anal catheter, penile ring or erectile function device, eye patch, vascular tube or catheter, hollow viscous catheter or tube, a seal for a surgical field which can be used to but not restricted to keeping the keeping a surgical field of infection or tumor from extending beyond its field, gloves, or clothing such as but not restricted to footwear or gloves.

In another embodiment the bridging or closure device can be used to adjust to the physiologic motions of the body that can include but are not restricted to connecting or bridging across or around joints or moving muscles or body part and structures and can also include serve as a transition between a biological structure and a non-biological structure such as but not restricted to between the thigh and a urinary bag, a cast and a cast cover.

In one embodiment the bridging or closure device is designed to make it easier to close or bridge or release or open one or more structures connected by the closure or bridging system. In on embodiment there can be one or more than one strand in which to create the closure. One embodiment can include but is not restricted to annular bands that have an incremental increase in their tension in which there are three annular bands. In one embodiment the bands can be color coded for tension and to assist with removal. The first band is yellow and has mild tension, the second band is green and has moderate tension and the third band is blue and has strong or intense tension in which the third band would represent a complete closure of the two apposing structures. To open the structure the process is reversed and the most tense band is removed first such that the intense tension blue band is removed then the moderate tension green band then the mild tension yellow band is removed. This embodiment can be used for but not restricted to a cast cover, a wound cover, a PIC line or vascular catheter cover, a urinary catheter bag, a penile ring, a condom catheter, an ostomy device, gloves, or footwear or clothing or tourniquet or for non-organic uses to include but not restricted to snow-chains, or closing a lid and this closure can be referred to as a transitional closure.

In another embodiment, each individual strand can also be composed such that the properties can include but are not restricted to movement, rotation, twisting, elasticity, stretchability, or malleability can vary within an individual or multiple strands. In one embodiment, the variation in properties can be from lamination or multilayered variability that can be continuous or discontinuous FLEX Design.

In another embodiment, the nosepiece can be attached to the eyepiece or the seal or the strap or any combination of these components.

One invention can include but is not restricted to a seal or a portion of a seal) that can create an airtight or watertight or acoustic seal with the user's skin or orifice or body lining that can be composed of a phase change material that can include but are not restricted to a non-encapsulated or an encapsulated PCMs that are macro-encapsulations, micro-encapsulations or a phase change slurry (PCS) that can create an airtight or watertight or acoustic seal with the user's skin or orifice or body lining. The seal can be used with a material that can include but is not restricted to a membrane or a frame or structure. The seal can be annular or non-annular or a combination of these elements. The PCM and PCS seal can be used for but not restricted to a seal for swimming goggles, a cast cover, a wound cover, a PIC Line cover, a respiratory or breathing mask to include but not restricted to a CPAP mask, a positive or negative pressure breathing mask, an intubation device, a male or female urinary condom catheter, ear buds, earphones, nose plugs, ostomy, an anal plug or anal catheter, penile ring or erectile function device, eye patch, vascular tube or catheter, hollow viscous catheter or tube, a seal for a surgical field which can be used to but not restricted to keeping the keeping a surgical field of infection or tumor from extending beyond its field or clothing such as but not restricted to footwear or gloves or pant bottoms.

Embodiments of the nosepiece can include the properties that include but are not restricted to being adjustable to the inter-pupillary distance, can be slipped on and off and changed more easily than current nosepieces, and is more secure than current nosepieces and does not fall off, multiple nosepiece shapes can be chosen and then these selected shapes have additional adjustment built in through elasticity and angulation and design shape that fits the nose, fits the nose contour and anatomy more comfortably than the current models, the nosepiece moves with the face/skin movements but the seal remains airtight and watertight, can create a universal kit that can work on multiple manufacturing company's goggle and therefore is not unique to only one specific pair of goggle, can be composed of multiple pieces (strands) that create greater contour and movement and fit, and the nosepiece attachment can have multiple locations on the eyepiece, the seal or the strap and can have variable angles and heights and shapes to better contour to the human anatomy of nose and the eye and can have a continuous strap and Nosepiece and the Closure device can flex and bend and simulate or mimic physiologic movements of muscles and joints such as the knee elbow shoulder and each closure can be designed for that specific joint.

Current static closures put the stress on the object being closed and not on the closure device and by using this principle the nosepieces creates a better form fitting goggle and seal.

In one embodiment, the eyepiece or the nosepiece can have an attachment component that can include an eyepiece that has an annular or centrally hollow aspect onto which the nosepiece can be attached and the annular or non annular extension that can include a curved shape or an angular shaped attachment element that can have one or more or less than one partition or division and can have one or more than one or less than one slit or passage that allows a connecting piece or bridge or nosepiece to pass through the slit or passage. In this embodiment there can be one or more than one attachment and the attachment can be on the nosepiece, the eyepiece or the strap.

In another embodiment, the attachment can be angled or elongated in a static or fixed manner or can dynamically elongate to improve the fit to contour better to the user's face an in one embodiment to include but not restricted to a telescoping elongating attachment.

In another embodiment, the eyepiece or nosepiece or strap that can be incorporated or have an attachment can have a swivel or ball-bearing-like device that can move in a manner to include but not restricted to swivel or rotate or move in an angular or curvilinear or spiral manner and can adjust to the energetic forces to include but not restricted to compression or pressures to adjust to the user's contours of the face/skin/body parts.

In another invention a fitting device can be used or incorporated into the choosing or into the creation of a better fitting of pair of goggles. Topographic 3-D mapping of the body is possible using multiple methods that include but are not restricted to direct physical contact with a physical substance such s a series of sliding pegs, physical measurements being placed into a computer or device, mechanical structures that conform to the topography of the face, foam or gel; or an energetic method for topographic 3-D mapping to include but not restricted to RGB scanning systems, laser scanning to include but not restricted to low level lasers, Magnetic resonance imaging, Ultrasound including but not restricted to A-mode, B-mode, C-mode, M-mode including but not restricted to Doppler, color Doppler, continuous mode, pulsed wave and Duplex, pulsed inversion mode, and harmonic mode; photogrammetry, and television scanning. The subject or user or the source of imaging can be rotated and the scan executed and the data collected and then analyzed using computer added design and reconstruction programs. This data can then be used to render a 3-D image of the face and can be used at home or at a manufacturing facility to customize a pair of goggles with a frame and seal and nosepiece and strap or any combination of these elements that precisely fits the face of the user who has been scanned, or can be used to choose from a series of goggles/mask and choose a 'best fit' pair of goggles/mask and this process can be performed at sites to include but not restricted to the home using a home computer and app, software program or device, a kiosk, or a wholesale or retail outlet or store.

In another embodiment the fitting device can be applied to uses other than just goggles and can include but is not restricted to swimming goggles, a cast cover, a wound cover, a PIC Line cover, a respiratory or breathing mask to include but not restricted to a CPAP mask, a positive or negative pressure breathing mask, an intubation device, a male or female urinary condom catheter, ear buds, earphones, nose plugs, ostomy, an anal plug or anal catheter, penile ring or erectile function device, eye patch, vascular tube or catheter, hollow viscous catheter or tube, a seal for a surgical field which can be used to but not restricted to keeping the keeping a surgical field of infection or tumor from extending beyond its field or clothing such as but not restricted to footwear or gloves.

In another embodiment the topographic contour can be used to calculate not just the external superficial contours but also can include internal contours or volumes. In one embodiment the surface contour can be used to render the shape of a body part and from this body part a rendered shape can be calculated that can then be used to determine the internal shape or size of a structure that will fit over that body part that can include but is not restricted to in one embodiment limb with a cast and from that topographic assessment a cast cover size and shape and volume can be approximated and the user can then choose the 'best fit' cast cover or can have a customized cast cover constructed to fit that individual user.

In one embodiment the cast cover size and shape can be constructed at the site to fit that patient. In one embodiment the cast cover can have at least one component that is a plastic bag that is annular and covers the surface of the user and the cast and in this embodiment one or more rolls of continuous hollow tubes can be present and when topographic measurements are calculated by a method to include but not restricted to a 3-D topographic mapping device or a mechanical device or simple measurements such as a but not restricted to a tape measure or ruler or placing the cast into a hollow tube or bag and once the user is measured a manufacturing device can be initiated and the manufacturing device can include but is not restricted to measuring out the hollow plastic tube and heat sealing one end and then cutting that sealed end off from the remainder of the hollow roll thus creating a cast cover that is tailored precisely for the user and the user's cast, or in another embodiment the machine that seals one end of the tube can also create a configuration that fits the hand/fingers or foot/toes of the user, or in another embodiment can create a tapered configuration to reduce redundant materials and yet allow the tube to fit over the cast or limb. Sealing the tube will depend on the material that is being used as a membrane or covering and in this embodiment the tube or membrane or covering is plastic the sealing process can include but is not restricted to heat sealing, glues or adhesives, stitching or electromagnetic or kinetic/mechanical forms of sealing to include but not restricted to radiofrequency, ultrasound or laser or welding.

In another embodiment the end product can be calculated from the topographical and volumetric or a combination of both elements data and can be manufactured by methods that can include but are not restricted to extrusion, surface molding or cutting to form a best fit product that can include but is not restricted to swimming goggles, a cast cover, a wound cover, a PIC Line cover, a respiratory or breathing mask to include but not restricted to a CPAP mask, a positive or negative pressure breathing mask, an intubation device, a male or female urinary condom catheter, ear buds, earphones, nose plugs, ostomy, an anal plug or anal catheter, penile ring or erectile function device, eye patch, vascular tube or catheter, hollow viscous catheter or tube, a seal for a surgical field which can be used to but not restricted to keeping the keeping a surgical field of infection or tumor from extending beyond its field or clothing such as but not restricted to footwear or gloves.

These methods and devices and inventions can also be used in human and non-human living creatures.

The methods for the testing devices can be used for other applications to include but not restricted to feet to include but not restricted to shoe and sock sizes; hands to include but not restricted to sizing gloves; head for hat and helmet sizes, mouth for mask sizes; body for shirt and dress and pants sizes.

The methods for the testing devices can analyze the information and patterns by using analog or digital methods that can include but are not restricted to charts, computers, visual inspection, automated analysis and non-automated analysis.

The methods for the testing devices can be applied to but not restricted to sizing an object, creating a user interface, determining the optimal thickness or requirements of an object to include but not restricted to optimal warmth, cooling, light, shade, sensitivity to touch, softness and hardness, stimulation of a body part, feedback for pain, touch, and temperature.

These methods and devices and inventions can also be used in human and non-human living creatures.

In compliance with the statute, the invention described herein has been described in language more or less specific as to structural features. It should be understood however, that the invention is not limited to the specific features shown, since the means and construction shown, is comprised only of the preferred embodiments for putting the invention into effect. The invention is therefore claimed in any of its forms or modifications within the legitimate and valid scope of the amended claims, appropriately interpreted in accordance with the doctrine of equivalents.

What is claimed is:

1. A pair of eye goggles, comprising:
    a three axial adjustable nosepiece that can be fit over a wearer's nose comprising a plurality of unequal length strands on each side of the nosepiece with the strands comprising resilient properties different from the resilient properties comprised in the other strands in the plurality of strands on that side;
    a strap that can be fit removably around the wearer's head; and a pair of eyepieces, each eyepiece comprising:
a transparent lens that can be fit over one of the wearer's eyes; and
a frame that surrounds the transparent lens to which the nosepiece and the strap are attached; and
a sealing pad formed on an inside-facing edge of the frame.

2. A pair of eye goggles in accordance with claim 1, further comprising:
a tester adapted to assist the user in choosing a 'best fit' pair of eye goggles comprising a gel that is sensitive to pressure, thickness and seal.

3. A pair of eye goggles in accordance with claim 2, wherein the gel is adapted to change color at different pressure points.

4. A pair of eye goggles in accordance with claim 2, wherein the tester is adapted to assess the 'best fit' pair of eye goggles in the form of a digital image.

5. A pair of eye goggles in accordance with claim 1, wherein the sealing pad is formed as an integral part of the strap.

6. A pair of eye goggles in accordance with claim 1, wherein the frame is formed as an integral part of the transparent lens.

7. A pair of eye goggles in accordance with claim 1, wherein the strap engageably and individually surrounds each of the frames of the pair of eyepieces.

8. A pair of eye goggles in accordance with claim 1, wherein the nosepiece further comprises a middle strand to which the plurality of unequal length strands on each side of the nosepiece are affixed with the middle strand comprising resilient properties different from the resilient properties comprised in the other strands in the plurality of strands on each side.

* * * * *